(12) United States Patent
Rivero et al.

(10) Patent No.: US 8,778,937 B2
(45) Date of Patent: Jul. 15, 2014

(54) BENZIMIDAZOLE BORONIC ACID DERIVATIVES AS PI3 KINASE INHIBITORS

(71) Applicant: GlaxoSmithKline LLC, Philadelphia, PA (US)

(72) Inventors: Ralph A. Rivero, Collegeville, PA (US); Rosanna Tedesco, Collegeville, PA (US); Juan Ignacio Luengo, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 124 days.

(21) Appl. No.: 13/674,202

(22) Filed: Nov. 12, 2012

(65) Prior Publication Data

US 2013/0157977 A1 Jun. 20, 2013

Related U.S. Application Data

(60) Provisional application No. 61/577,907, filed on Dec. 20, 2011.

(51) Int. Cl.
| | |
|---|---|
| *C07D 413/10* | (2006.01) |
| *A61K 31/535* | (2006.01) |
| *C07D 413/04* | (2006.01) |
| *C07D 417/10* | (2006.01) |
| *C07F 5/02* | (2006.01) |

(52) U.S. Cl.
CPC ............. *C07F 5/025* (2013.01); *C07D 417/10* (2013.01)
USPC ........................................ 514/234.5; 544/139

(58) Field of Classification Search
USPC ........................................ 544/139; 514/234.5
See application file for complete search history.

(56) References Cited

U.S. PATENT DOCUMENTS

| 5,502,187 | A  * | 3/1996 | Ayer et al. ...................... 544/117 |
| 7,223,757 | B2 * | 5/2007 | Wittman et al. ............ 514/235.8 |
| 8,435,988 | B2 * | 5/2013 | Qu et al. .................... 514/234.5 |

* cited by examiner

*Primary Examiner* — Rebecca Anderson
(74) *Attorney, Agent, or Firm* — J. Scott Young

(57) ABSTRACT

This invention relates to the use of benzimidazole boronic acid derivatives for the modulation, notably the inhibition of the activity or function of the phosphoinositide 3' OH kinase family (hereinafter PI3 kinases), suitably, PI3Kα, PI3Kδ, PI3Kβ, and/or PI3Kγ. Suitably, the present invention relates to the use of benzimidazole boronic acids in the treatment of one or more disease states selected from: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries. More suitably, the present invention relates to PI3Kβ selective benzimidazole boronic acid compounds for treating cancer.

9 Claims, No Drawings

BENZIMIDAZOLE BORONIC ACID DERIVATIVES AS PI3 KINASE INHIBITORS

FIELD OF THE INVENTION

This invention relates to the use of benzimidazole boronic acid derivatives for the modulation, notably the inhibition of the activity or function of the phosphoinositide 3' OH kinase family (hereinafter PI3 kinases), suitably, PI3Kα, PI3Kδ, PI3Kβ, and/or PI3Kγ. Suitably, the present invention relates to the use of benzimidazole boronic acids in the treatment of one or more oncologic disorders. More suitably, the present invention relates to PI3Kβ selective benzimidazole boronic acid compounds for treating cancer.

BACKGROUND OF THE INVENTION

The phosphoinositide 3-kinase (PI3K) pathway is among the most commonly activated in human cancer and the importance in carcinogenesis is well established (Samuels Y and Ericson K. Oncogenic PI3K and its role in cancer. *Current Opinion in Oncology,* 2006; 18:77-82). Initiation of signaling begins with the phosphorylation of phosphatidylinositol-4,5-bisphosphate (PIP2) to produce phosphatidylinositol-3,4,5-P3 (PIP3). PIP3 is a critical second messenger which recruits proteins that contain pleckstrin homology domains to the cell membrane where they are activated. The most studied of these proteins is AKT which promotes cell survival, growth, and proliferation.

The PI3K family consists of 15 proteins that share sequence homology, particularly within their kinase domains, but have distinct substrate specificities and modes of regulation (Vivanco I and Sawyers C L. The phosphatidylinositol 3-kinase-AKT pathway in human cancer. *Nature Reviews Cancer,* 2002; 2:489-501). Class I PI3Ks are heterodimers consisting of a p110 catalytic subunit complexed to one of several regulatory subunits collectively referred to as p85 and have been the most extensively studied in the context of tumorgenesis. The class 1A PI3K catalytic subunits comprise the p110α, p110β, and p110δ isoforms, which associate with one of five different regulatory subunits encoded by three separate genes. A single class 1B PI3K catalytic isoform p110γ interacts with one of two associated regulatory subunits (Crabbe T, Welham M J, Ward S G, The PI3k inhibitor arsenal: choose your weapon *Trends in Biochem Sci,* 2007; 32:450-456). Class 1 PI3Ks are primarily responsible for phosphorylating the critical PIP2 signaling molecule.

The link between the PI3K pathway and cancer was confirmed by a study which identified somatic mutations in the PIK3CA gene encoding the p110α protein. Subsequently, mutations in PIK3CA have been identified in numerous cancers including colorectal, breast, glioblastomas ovarian and lung. In contrast to PIK3CA, no somatic mutations in the β isoform have been identified. However, in overexpression studies, the PI3Kβ isoform has been implicated as necessary for transformation induced by the loss or inactivation of the PTEN tumor suppressor both in vitro and in vivo (Torbett N E, Luna A, Knight Z A, et al., A chemical screen in diverse breast cancer cell lines reveals genetic enhancers and suppressors of sensitivity to PI3K isotype-selective inhibition. *Biochem J* 2008; 415:97-110; Zhao J J, Liu Z, Wang L, Shin E, Loda M F, Roberts T M, The oncogenic properties of mutant p110a and p110b phosphatidylinositol 3-kinases in human mammary epithelial cells. *Proc Natl Acad Sci USA* 2005; 102:18443-8). Consistent with this finding, overexpression of the PIK3CB gene has been identified in some bladder, colon, glioblastomas and leukemias and siRNA mediated knock-down of p110β in glioblastoma cell lines results in suppression of tumor growth in vitro and in vivo (Pu P, Kang C, Zhang Z, et al., Downregulation of PIK3CB by siRNA suppresses malignant glioma cell growth in vitro and in vivo. *Technolo Cancer Res Treat* 2006; 5:271-280). More recent data using shRNA demonstrated that downregulation of p110β and not p110α resulted in PI3K pathway inactivation and subsequent inactivation of tumor cell growth in PTEN deficient cancers cells both in vitro and in vivo (Wee S, Wiederschain, Maira S-M, Loo A, Miller C, et al., PTEN-deficient cancers depend on PIK3CB. *Proc Natl Acad Sci* 2008; 105:13057-13062). Consistent with a role of PIK3CB signaling in PTEN null tumors, p110β was reported to be essential to the transformed phenotype in a PTEN-null prostate cancer model (Jia S, Liu Z, Zhang S, Liu P, Zhang L, et al., Essential roles of PI(3)K-p110b in cell growth, metabolism and tumorgenesis. *Nature* 2008; 10:1038).

Further, it has been reported that fibrogenesis, including systemic sclerosis (SSc), arthritis, nephropahty, liver cirrhosis, and some cancers, are related to PTEN deficiency and corresponding PI3K-Akt overexpression (Parapuram, S. K., et al., Loss of PTEN expression by dermal fibroblasts causes skin fibrosis. J. of Investigative Dermatology, advance online publication 9 Jun. 2011; doi: 10.1038/jid.2011.156). Taken together, these findings indicate PI3K p110β as a promising target for cancer and other syndromes related to PTEN loss (Hollander, M. Christine; Blumenthal, Gideon M.; Dennis, Phillip P.; PTEN loss in the continuum of common cancers, rare syndromes and mouse models. *Nature Reviews/Cancer* 2011; 11: 289-301). It is therefore desirable to create a potent, selective inhibitor of PI3K-β.

SUMMARY OF THE INVENTION

This invention relates to novel compounds of formula (I):

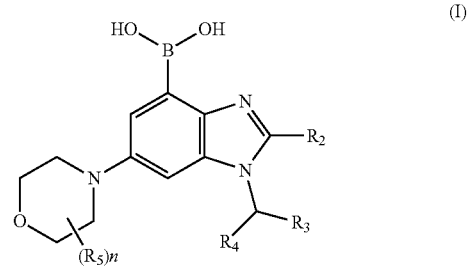

wherein
R2 is selected from H, —NHRa, alkoxy, halogen, —CF$_3$, —CHF$_2$, and C$_{1-6}$alkyl;
R3 is selected from aryl and heteroaryl, wherein said aryl or heteroaryl may be substituted by one to three Rc;
R4 is selected from H or Ra;
each R5 is independently selected from C$_{1-6}$alkyl;
each Ra is independently selected from C$_{1-3}$alkyl;
each Rc is independently selected from C$_{1-3}$alkyl, halogen, —CF$_3$, and hydroxy; and
n is 0-2,
or a pharmaceutically acceptable salt thereof.

In another aspect of the present invention, there is provided a method of treating a susceptible neoplasm in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a compound of formula (I), (including any particular sub-generic formula described herein) or a pharmaceutically acceptable salt thereof for use in therapy.

In another aspect, there is provided a compound of formula (I) (including any particular sub-generic formula described herein) or a pharmaceutically acceptable salt thereof for use in the treatment of a susceptible neoplasm in a mammal in need thereof.

In a another aspect of the present invention, there is provided the use of a compound of formula (I) (including any particular sub-generic formula described herein) or a pharmaceutically acceptable salt thereof, in the preparation of a medicament for use in the treatment of a susceptible neoplasm in a mammal in need thereof.

In another aspect of the present invention, there is provided a pharmaceutical composition comprising a compound of formula (I) (including any particular sub-generic formula described herein) or a pharmaceutically acceptable salt thereof for use in the treatment of a susceptible neoplasm in a mammal in need thereof.

DETAILED DESCRIPTION OF THE INVENTION

This invention is directed to compounds of Formula (I).

According to another embodiment, the invention includes the compounds of Formula (I)(A)

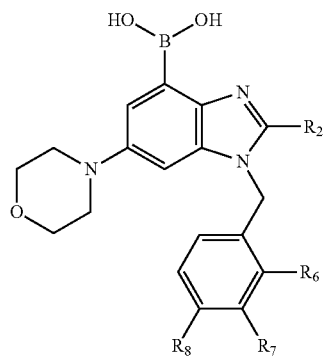

(I)(A)

wherein

R2 is selected from H, —NHRa, alkoxy, —CH$_2$Rc, —CH(Rc)$_2$, —CF$_3$, or C$_{1-6}$alkyl;

each of R6, R7, and R8 is independently selected from C$_{1-3}$alkyl, halogen, —CF$_3$, and hydroxyl, or R6 and R7 combine to form a bi-cyclic aryl or heteroaryl, or R7 and R8 combine to form a bi-cyclic aryl or heteroaryl;

each Ra is independently selected from C$_{1-3}$alkyl; and each Rc is selected from CH$_3$ and F;

or a pharmaceutically acceptable salt thereof.

According to another embodiment, the invention includes the compounds of Formula (I)(B)

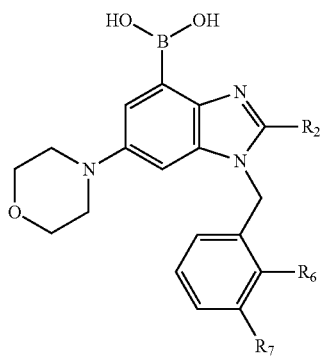

(I)(B)

wherein

R2 is selected from H, —CH$_2$Rc, —CH(Rc)$_2$, —CF$_3$, or C$_{1-6}$ alkyl;

each of R6 and R7 is independently selected from C$_{1-3}$ alkyl, halogen, and —CF$_3$, or R6 and R7 combine to form a bi-cyclic aryl or heteroaryl; and each Rc is selected from CH$_3$ and F;

or a pharmaceutically acceptable salt thereof.

According to another embodiment, the invention includes compounds of formula (I)(B) wherein R6 and R7 combine to form a naphthal or an indole.

According to another embodiment, the invention includes compounds of formula (I)(B) wherein R6 and R7 are independently selected from C$_{1-3}$ alkyl, halogen, and —CF$_3$.

According to another embodiment, the invention includes compounds:

4-(4-bromo-2-methyl-1H-benzo[d]imidazol-6-yl)morpholine;
4-(4-bromo-1-(3-chloro-2-methylbenzyl)-2-methyl-1H-benzo[d]imidazol-6-yl)morpholine;
4-(4-bromo-2-methyl-1-(2-methyl-3-(trifluoromethyl)benzyl)-1H-benzo[d]imidazol-6-yl)morpholine;
(2-methyl-1-(2-methyl-3-(trifluoromethyl)benzyl)-6-morpholino-1H-benzo[d]imidazol-4-yl)boronic acid;
(1-(3-chloro-2-methylbenzyl)-2-methyl-6-morpholino-1H-benzo[d]imidazol-4-yl)boronic acid;
(2-methyl-6-morpholino-1-(naphthalen-1-ylmethyl)-1H-benzo[d]imidazol-4-yl)boronic acid;
(1-(2,3-dimethylbenzyl)-2-methyl-6-morpholino-1H-benzo[d]imidazol-4-yl)boronic acid;
(1-(2,3-dichlorobenzyl)-2-methyl-6-morpholino-1H-benzo[d]imidazol-4-yl)boronic acid;
4-(1-(benzo[b]thiophen-7-ylmethyl)-4-bromo-2-methyl-1H-benzo[d]imidazol-6-yl)morpholine;
(2-methyl-1-(3-methylbenzyl)-6-morpholino-1H-benzo[d]imidazol-4-yl)boronic acid;
(2-methyl-1-(2-methylbenzyl)-6-morpholino-1H-benzo[d]imidazol-4-yl)boronic acid;
(1-(2-chlorobenzyl)-2-methyl-6-morpholino-1H-benzo[d]imidazol-4-yl)boronic acid;
(1-(3-chlorobenzyl)-2-methyl-6-morpholino-1H-benzo[d]imidazol-4-yl)boronic acid;
(1-(2-methyl-3-(trifluoromethyl)benzyl)-6-morpholino-1H-benzo[d]imidazol-4-yl)boronic acid;
(1-(3-chloro-2-methylbenzyl)-6-morpholino-1H-benzo[d]imidazol-4-yl)boronic acid;
(2-(fluoromethyl)-1-(2-methyl-3-(trifluoromethyl)benzyl)-6-morpholino-1H-benzo[d]imidazol-4-yl)boronic acid;
(1-(3-chloro-2-methylbenzyl)-2-(fluoromethyl)-6-morpholino-1H-benzo[d]imidazol-4-yl)boronic acid;

(2-(hydroxymethyl)-1-(2-methyl-3-(trifluoromethyl)benzyl)-6-morpholino-1H-benzo[d]imidazol-4-yl)boronic acid;
(1-(3-chloro-2-methylbenzyl)-2-(difluoromethyl)-6-morpholino-1H-benzo[d]imidazol-4-yl)boronic acid;
(2-(difluoromethyl)-1-(2-methyl-3-(trifluoromethyl)benzyl)-6-morpholino-1H-benzo[d]imidazol-4-yl)boronic acid;
(1-(3-chloro-2-methylbenzyl)-6-morpholino-2-(trifluoromethyl)-1H-benzo[d]imidazol-4-yl)boronic acid;
(2-isopropyl-1-(2-methyl-3-(trifluoromethyl)benzyl)-6-morpholino-1H-benzo[d]imidazol-4-yl)boronic acid; and
(2-cyclopropyl-1-(2-methyl-3-(trifluoromethyl)benzyl)-6-morpholino-1H-benzo[d]imidazol-4-yl)boronic acid.

DEFINITIONS

By the term "aryl" as used herein, unless otherwise defined, is meant aromatic, hydrocarbon, ring system. The ring system may be monocyclic or fused polycyclic (e.g. bicyclic, tricyclic, etc.). In various embodiments, the monocyclic aryl ring is C5-C10, or C5-C7, or C5-C6, where these carbon numbers refer to the number of carbon atoms that form the ring system. A C6 ring system, i.e. a phenyl ring is a suitable aryl group. In various embodiments, the polycyclic ring is a bicyclic aryl group, where suitable bicyclic aryl groups are C8-C12, or C9-C10. A naphthyl ring, which has 10 carbon atoms, is a suitable polycyclic aryl group.

By the term "heteroaryl" as used herein, unless otherwise defined, is meant an aromatic ring system containing carbon(s) and at least one heteroatom. Heteroaryl may be monocyclic or polycyclic. A monocyclic heteroaryl group may have 1 to 4 heteroatoms in the ring, while a polycyclic heteroaryl may contain 1 to 10 hetero atoms. A polycyclic heteroaryl ring may contain fused, spiro or bridged ring junctions, for example, bicyclic heteroaryl is a polycyclic heteroaryl. Bicyclic heteroaryl rings may contain from 8 to 12 member atoms. Monocyclic heteroaryl rings may contain from 5 to 8 member atoms (carbons and heteroatoms). Exemplary heteroaryl groups include: benzofuran, benzothiene, benzothiophene, furan, imidazole, indole, isothiazole, oxazole, pyrazine, pyrazole, pyridazine, pyridine, pyrimidine, pyrrole, quinoline, isoquinoline, quinazoline, quinoxaline, thiazole, and thiophene. According to an alternative embodiment, heteroaryls may be substituted with one to three alkyl groups.

By the term "alkoxy" as used herein is meant —O(alkyl) including —OCH$_3$, —OCH$_2$CH$_3$ and —OC(CH$_3$)$_3$ where alkyl is as described herein.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein, including alkyl chains defined by the term "—(CH$_2$)$_n$—", "—(CH$_2$)$_m$—" and the like, is meant a linear or branched, saturated or unsaturated hydrocarbon chain, and unless otherwise defined, the carbon chain will contain from 1 to 12 carbon atoms.

By the term "co-administering" and derivatives thereof as used herein is meant either simultaneous administration or any manner of separate sequential administration of a PI3 kinase inhibiting compound, as described herein, and a further active ingredient or ingredients. The term further active ingredient or ingredients, as used herein, includes any compound or therapeutic agent known to or that demonstrates advantageous properties when administered to a patient in need of treatment. Suitably, if the administration is not simultaneous, the compounds are administered in a close time proximity to each other. Furthermore, it does not matter if the compounds are administered in the same dosage form, e.g. one compound may be administered topically and another compound may be administered orally.

The term "compound" as used herein includes all isomers of the compound. Examples of such isomers include: enantiomers, tautomers, rotamers.

Certain compounds described herein may contain one or more chiral atoms, or may otherwise be capable of existing as two enantiomers, or two or more diastereoisomers. Accordingly, the compounds of this invention include mixtures of enantiomers/diastereoisomers as well as purified enantiomers/diastereoisomers or enantiomerically/diastereoisomerically enriched mixtures. Also included within the scope of the invention are the individual isomers of the compounds represented by Formula (I) above as well as any wholly or partially equilibrated mixtures thereof. The present invention also covers the individual isomers of the compounds represented by the formulas above as mixtures with isomers thereof in which one or more chiral centers are inverted. The present invention also includes isotopomers of the compounds of Formula (I). Examples of such isotopomers include but not limited to compounds with one of more deuterium atoms.

It will be appreciated by those skilled in the art that the compounds of formula (I) may be utilized as a pharmaceutically acceptable salt version thereof. The pharmaceutically acceptable salts of the compounds of formula (I) include conventional salts formed from pharmaceutically acceptable (i.e., non-toxic) inorganic or organic acids or bases as well as quaternary ammonium salts. Representative salts include the following: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, ethanol amine, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate (methanesulfonate), methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate(methylbenzenesulfonate), triethiodide, trimethylammonium and valerate. Other salts, such as oxalic and trifluoroacetic, which are not themselves pharmaceutically acceptable, may be useful in the preparation of salts useful as intermediates in obtaining compounds of this invention and these form a further aspect of the invention. In one embodiment, the compound of formula (I) is in the form of the free base. In one embodiment, the compound of formula (I) is in the form of the sodium salt. Certain salt versions of the compounds may be solvates, particularly hydrates. In one embodiment, the compound of formula (I) or a pharmaceutically acceptable salt thereof is in the form of a mono-, di-, tri- or hemi-hydrate.

It has now been found that compounds of the present invention are inhibitors of the Phosphatoinositides 3-kinases (PI3Ks). When the phosphatoinositides 3-kinase (PI3K) enzyme is inhibited by a compound of the present invention, PI3K is unable to exert its enzymatic, biological and/or pharmacological effects. The compounds of the present invention are therefore useful in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

Compounds according to Formula (I) are suitable for the modulation, notably the inhibition of the activity of phosphatoinositides 3-kinases (PI3K) and, more particularly, selective inhibitors of the beta isoform of phosphatoinositides 3-kinase (PI3Kβ). Therefore the compounds of the present invention are also useful for the treatment of disorders which are mediated by PI3Ks. Said treatment involves the modulation—notably the inhibition or the down regulation—of the phosphatoinositides 3-kinases.

Because the pharmaceutically active compounds of the present invention are active as PI3 kinase inhibitors, particularly the compounds that inhibit PI3Kβ, either selectively or in conjunction with one or more of PI3Kδ, PI3Kα, and/or PI3Kγ, they exhibit therapeutic utility in treatment of susceptible neoplasms, particularly those neoplasms that exhibit a PTEN deficiency.

As used herein, the phrase "PTEN deficient" or "PTEN deficiency" shall describe tumors with deficiencies of the tumor suppressor function of PTEN (Phosphatase and Tensin Homolog). Such deficiency includes mutation in the PTEN gene, reduction or absence of PTEN proteins when compared to PTEN wild-type, or mutation or absence of other genes that cause suppression of PTEN function.

As used herein, the term "treatment" or "treating" in the context of therapeutic methods, refers to alleviating the specified condition, eliminating or reducing the symptoms of the condition, slowing or eliminating the progression, invasion, or metastatic spread of the condition and preventing or delaying the reoccurrence of the condition in a previously afflicted subject. The present invention further provides use of the compounds of the invention for the preparation of a medicament for the treatment of several conditions in a mammal (e.g., human) in need thereof.

"Susceptible neoplasm" as used herein refers to neoplasms which are susceptible to treatment by a kinase inhibitor and particularly neoplasms that are susceptible to treatment by a PI3Kβ inhibitor. Neoplasms which have been associated with inappropriate activity of the PTEN phosphatase and particularly neoplasms which are exhibit mutation of PTEN, or mutation of an upstream activator of PI3Kβ kinase or overexpression of an upstream activator of PI3Kβ kinase, and are therefore susceptible to treatment with an PI3Kβ inhibitor are known in the art, and include both primary and metastatic tumors and cancers. According to one embodiment, description of the treatment of a susceptible neoplasm may be used interchangeably with description of the treatment of a cancer.

According to one embodiment, "susceptible neoplasms" includes, but are not limited to PTEN-deficient neoplasms listed as follows:
brain (gliomas),
glioblastomas,
leukemias,
Bannayan-Zonana syndrome,
Cowden disease,
Lhermitte-Duclos disease,
breast cancer,
inflammatory breast cancer,
colorectal cancer
Wilm's tumor,
Ewing's sarcoma,
Rhabdomyosarcoma,
ependymoma,
medulloblastoma,
colon cancer,
head and neck cancer,
kidney cancer,
lung cancer,
liver cancer,
melanoma,
squamous cell carcinoma,
ovarian cancer,
pancreatic cancer,
prostate cancer,
sarcoma cancer,
osteosarcoma,
giant cell tumor of bone,
thyroid cancer,
lymphoblastic T cell leukemia,
chronic myelogenous leukemia,
chronic lymphocytic leukemia,
hairy-cell leukemia,
acute lymphoblastic leukemia,
acute myelogenous leukemia,
chronic neutrophilic leukemia,
acute lymphoblastic T cell leukemia,
Plasmacytoma,
Immunoblastic large cell leukemia,
Mantle cell leukemia,
Multiple myeloma,
Megakaryoblastic leukemia,
multiple myeloma,
Acute megakaryocytic leukemia,
promyelocytic leukemia,
Erythroleukemia,
malignant lymphoma,
hodgkins lymphoma,
non-hodgkins lymphoma,
lymphoblastic T cell lymphoma,
Burkitt's lymphoma,
follicular lymphoma,
neuroblastoma,
bladder cancer,
urothelial cancer,
vulval cancer,
cervical cancer,
endometrial cancer,
renal cancer,
mesothelioma,
esophageal cancer,
salivary gland cancer,
hepatocellular cancer,
gastric cancer,
nasopharangeal cancer,
buccal cancer,
cancer of the mouth,
GIST (gastrointestinal stromal tumor),
and testicular cancer.

According to an alternative embodiment, the term "susceptible neoplasm" includes and is limited to hormone refractory prostate cancer, non-small-cell lung cancer, endometrial cancer, gastric cancer, melanoma, head and neck cancer, breast cancer, including trip-negative breast cancer, and glioma. PTEN deficiency has been correlated to such cancers as demonstrated in a number of published resources, e.g. Am J Clin Pathol. 2009 February; 131(2):257-63 (glioblastoma), J Clin Neurosci. 2010 December; 17(12): 1543-7 (glioblastoma), Nat. Genet. 2009 May; 41(5):619-24 (prostate cancer), Br J Cancer. 2008 Oct. 21; 99(8):1296-301 (prostate cancer), Int J Cancer. 2007 Mar. 15; 120(6):1284-92 (prostate cancer), J Invest Dermatol. 2006 January; 126(1):154-60 (melanoma), J Clin Oncol. 2006 Jan. 10; 24(2):288-95 (melanoma), Am J Clin Pathol. 2005 October; 124(4):528-36 (melanoma), Int J Oncol. 2009 April; 34(4):983-93 (breast cancer), Epigenetics. 2011 May 1; 6(5):638-49 (breast cancer), Gynecol Oncol. 2009 February; 112(2):307-13 (ovarian cancer), Mod Pathol. 2010 October; 23(10):1316-24 (ovarian cancer), J Pathol. 2010 February; 220(3):392-400 (ovarian cancer), Lung. 2009 March-April; 187(2):104-9 (lung cancer), Anticancer Res. 2007 January-February; 27(1B):575-81 (lung cancer), Am J Surg. 2008 June; 195(6):719-25 (colon cancer), J Clin Oncol. 2009 Dec. 10; 27(35):5924-30 (colon cancer), Gynecol Oncol. 2004 June; 93(3):621-7 (cervical cancer), and J Oral Pathol Med. 2002 August; 31(7):379-84 (head and neck cancer).

In another aspect of the present invention, there is provided a method of treating a susceptible neoplasm in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating fibrosis in a mammal in need thereof, comprising administering to the mammal a therapeutically effective amount of a compound of formula (I) (including any particular sub-generic formula described herein) or a pharmaceutically acceptable salt thereof. Fibrosis includes, alternatively or collectively, systemic sclerosis (SSc), arthritis, nephropahty, and liver cirrhosis.

In another aspect of the present invention, there is provided a method of treating hormone refractory prostate cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating non-small-cell lung cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating endometrial cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating gastric cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating melanoma in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating head and neck cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating trip-negative breast cancer in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a method of treating glioma in a mammal in need thereof, comprising administering to the mammal a therapeutically effective amount of a compound of formula (I) (including any particular sub-generic formula described herein) or a pharmaceutically acceptable salt thereof.

In another aspect of the present invention, there is provided a compound of formula (I), (including any particular sub-generic formula described herein) or a pharmaceutically acceptable salt thereof for use in therapy.

In another aspect, there is provided a compound of formula (I) (including any particular sub-generic formula described herein) or a pharmaceutically acceptable salt thereof for use in the treatment of a susceptible neoplasm in a mammal in need thereof.

In a another aspect of the present invention, there is provided the use of a compound of formula (I) (including any particular sub-generic formula described herein) or a pharmaceutically acceptable salt thereof, in the preparation of a medicament for use in the treatment of a susceptible neoplasm in a mammal in need thereof.

In another aspect of the present invention, there is provided a pharmaceutical composition comprising a compound of formula (I) (including any particular sub-generic formula described herein) or a pharmaceutically acceptable salt thereof for use in the treatment of a susceptible neoplasm in a mammal in need thereof.

When a compound of Formula (I) is administered for the treatment of cancer, the term "co-administering" and derivatives thereof as used herein is meant either simultaneous administration or any manner of separate sequential administration of a PI3 kinase inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients for use in combination or co-administered with the present PI3 kinase inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2/M$ phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-II-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem., Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl. Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxy, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is prima-rily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of Streptomyces verticillus, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2(1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl] methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

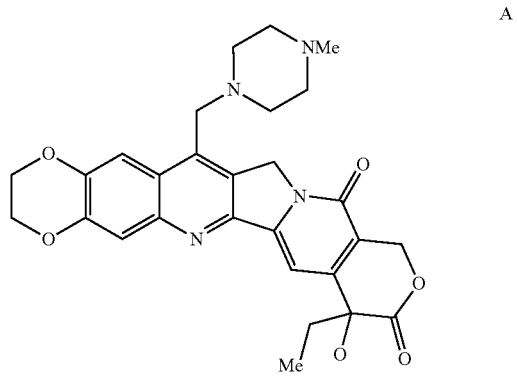 [SMILES: CCC1(O)C(=O)OCc2c1cc1n(c2=O)Cc2c-1nc1cc3c(cc1c2CN1CCN(C)CC1)OCCO3]

known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by overexpression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, AKT kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in the present invention are Myo-inositol signaling inhibitors such as phospholipase C blockers and Myo-inositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChem. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2Activity by a monoclonal Anti-VEGF antibody blocks tumor growth in mice, Cancer Res. (2000) 60, 5117-5124).

Non-receptor kinase angiogenesis inhibitors may also find use in the present invention. Inhibitors of angiogenesis related VEGFR and TIE2 are discussed above in regard to signal transduction inhibitors (both receptors are receptor tyrosine kinases). Accordingly, non-receptor tyrosine kinase inhibitors may be used in combination with the inhibitors of the present invention. For example, anti-VEGF antibodies, which do not recognize VEGFR (the receptor tyrosine kinase), but bind to the ligand; small molecule inhibitors of integrin (alpha beta$_3$) that will inhibit angiogenesis; endostatin and angiostatin (non-RTK) may also prove useful in combination with the disclosed family inhibitors. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of formula (I). There are a number of immunologic strategies to generate an immune response against erbB2 or EGFR. These strategies are generally in the realm of tumor vaccinations. The efficacy of immunologic approaches may be greatly enhanced through combined inhibition of erbB2/EGFR signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of formula I and/or a pharmaceutically acceptable salt, hydrate, solvate or pro-drug thereof and at least one antineoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of a PI3K inhibitor, the selected dose is administered preferably from 1-6 times daily, orally or parenterally. Preferred forms of parenteral administration include topically, rectally, transdermally, by injection and continuously by infusion. Oral dosage units for human administration preferably contain from 0.05 to 3500 mg of active compound. According to one embodiment, the oral dosage for human administration contains 100 to 1000 mg per day. Oral administration, which uses lower dosages is preferred. Parenteral administration, at high dosages, however, also can be used when safe and convenient for the patient.

Optimal dosages to be administered may be readily determined by those skilled in the art, and will vary with the particular PI3 kinase inhibitor in use, the strength of the preparation, the mode of administration, and the advancement of the disease condition. Additional factors depending on the particular patient being treated will result in a need to adjust dosages, including patient age, weight, diet, and time of administration. Exemplary dosages include oral formulations equivalent to 10 mg, 25 mg, and 100 mg of the compound of formula (I), to be administered alone, in multiples, or in combination.

The method of this invention of inducing PI3 kinase inhibitory activity in mammals, including humans, comprises administering to a subject in need of such activity an effective PI3 kinase modulating/inhibiting amount of a pharmaceutically active compound of the present invention.

The invention also provides for the use of a compound of Formula (I) in the manufacture of a medicament for use as a PI3 kinase inhibitor.

The invention also provides for the use of a compound of Formula (I) in the manufacture of a medicament for use in therapy.

The invention also provides for the use of a compound of Formula (I) in the manufacture of a medicament for use in treating autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries.

The invention also provides for a pharmaceutical composition for use as a PI3 inhibitor which comprises a compound of Formula (I) and a pharmaceutically acceptable carrier.

The invention also provides for a pharmaceutical composition for use in the treatment of autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries, which comprises a compound of Formula (I) and a pharmaceutically acceptable carrier.

In addition, the pharmaceutically active compounds of the present invention can be co-administered with further active ingredients, including compounds known to have utility when used in combination with a PI3 kinase inhibitor.

Without further elaboration, it is believed that one skilled in the art can, using the preceding description, utilize the present invention to its fullest extent. The following examples are, therefore, to be construed as merely illustrative and not a limitation of the scope of the present invention in any way.

Compounds of Formula (I) may be prepared using the general schemes, as described below.

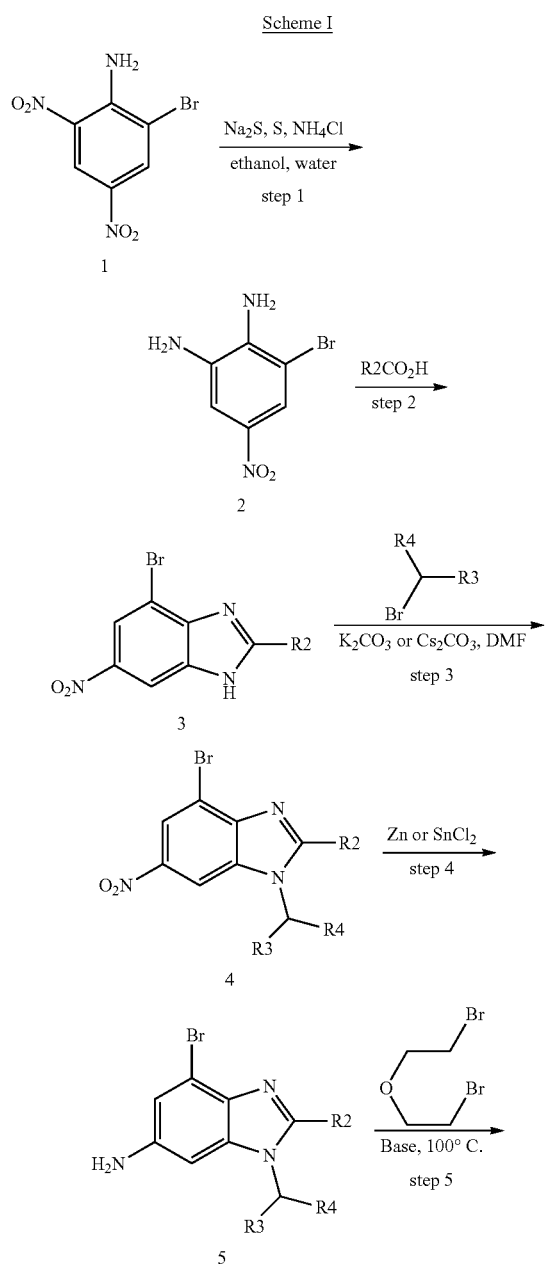

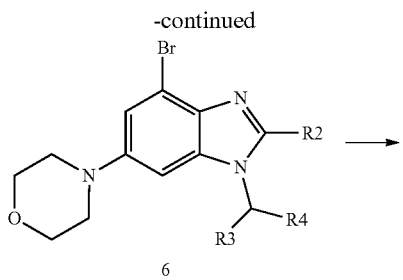

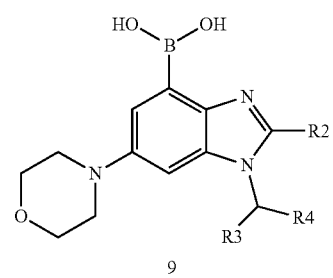

Sulfur-mediated reduction of 2-bromo-4,6-dinitroaniline in ethanol/water at elevated temperatures provides 2-amino-6-bromo-4-nitroaniline (2) which can be condensed with a variety of carboxylic acids ($R2CO_2H$) to provide 4-bromo-2-substituted-6-nitro-1H-benzo[d]imidazoles 3. Alkylation with a variety of alkyl halides in the presence of $K_2CO_3$ or $Cs_2CO_3$ in a polar aprotic solvent like DMF can provide tetra-substituted benzimidazole 4. Reduction of the nitro-group can be accomplished in the presence of $SnCl_2$ in MeOH or Zn in acetic acid to afford amino benzimidazole 5 that can subsequently be converted to the morpholine derivative 6 through reaction with 1-bromo-2-(2-bromoethoxy)ethane. Boronylation of 6 to generate benzimdazole boronic acid 9 can be accomplished either by Method A, metal-halogen exchange at −78 C with nbutyl-lithium in THF, followed by quenching with an appropriate boronate ester, or by Method B, Palladium catalyzed boronylation using bis(pinacolato)diboron and $Pd_2(dba)_3$ in a polar aprotic solvent like 1,4-dioxane at elevated temperatures.

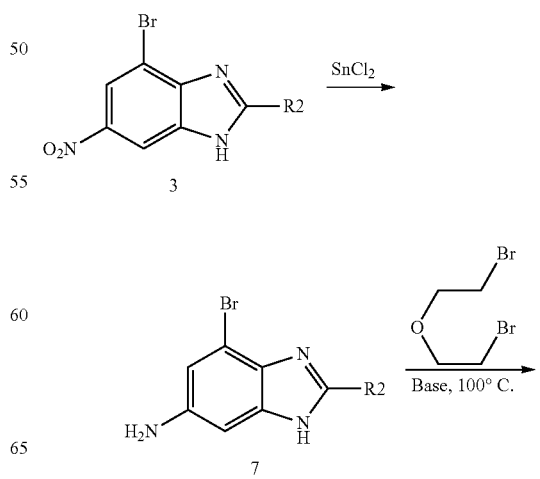

-continued

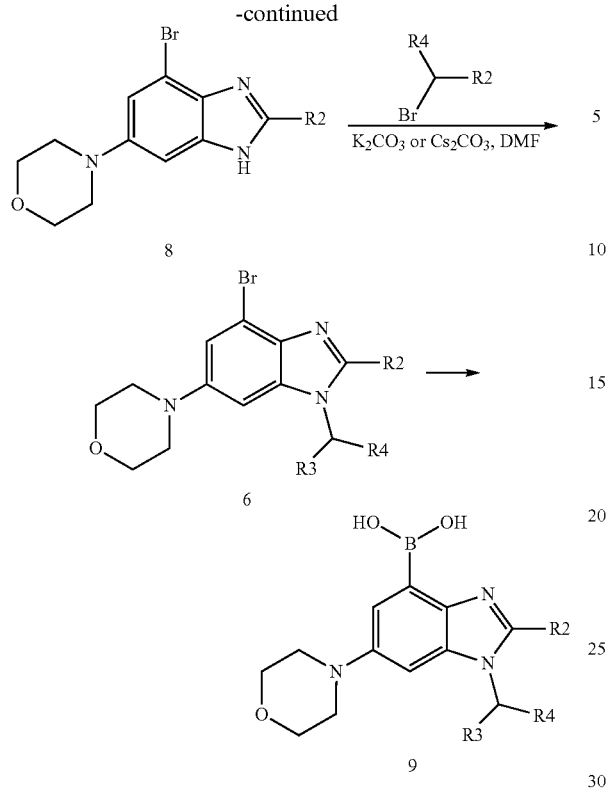

4-bromo-2-substituted-6-nitro-1H-benzo[d]imidazoles 3 can be reduced with SnCl$_2$ in MeOH to provide 4-bromo-6-amino benzimidazole 7 that can be subsequently converted to the morpholine derivative 8 through reaction with 1-bromo-2-(2-bromoethoxy)ethane. Alkylation with a variety of alkyl halides in the presence of K$_2$CO$_3$ or Cs$_2$CO$_3$ in a polar aprotic solvent like DMF can provide tetra-substituted benzimidazole 6. Boronylation of 6 to generate benzimdazole boronic acid 9 can be accomplished either by Method A, metal-halogen exchange at –78 C with nbutyl-lithium in THF, followed by quenching with an appropriate boronate ester, or by Method B, Palladium catalyzed boronylation using bis(pinacolato)diboron and Pd$_2$(dba)$_3$ in a polar aprotic solvent like 1,4-dioxane at elevated temperatures.

Various substituents used herein but not specifically exemplified may be found in the literature such as, for example, International Patent Publication WO2012/047538, incorporated herein by reference.

EXPERIMENTAL PROCEDURES

Example 1

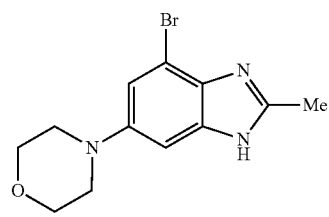 [SMILES: Cc1nc2c(Br)cc(N3CCOCC3)cc2[nH]1]

Preparation of 4-(4-bromo-2-methyl-1H-benzo[d]imidazol-6-yl)morpholine a) 4-bromo-2,6-dinitrobenzenamine

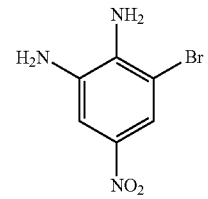 [SMILES: Nc1cc([N+](=O)[O-])cc(Br)c1N]

A mixture of sodium sulfide nonahydrate (96 g, 400 mmol) and sulfur (12.8 g, 400 mmol) in a mixture of 400 mL of water and 100 mL of ethanol was heated at reflux under nitrogen for 1 h. The solution was added to a stirred suspension of 2-bromo-4,6-dinitrobenzenamine (104.8 g, 400 mmol) and ammonium chloride (20.8 g, 400 mmol) in a mixture of 400 mL of water and 700 mL of ethanol. The mixture was stirred at 65° C. for 30 min. Then 400 mL of 2N NaOH solution was added dropwise during a period of 30 min and the mixture was then stirred for a further 15 minutes at 65° C. After cooling, the mixture was poured onto a mixture of 2N HCl (400 mL), 1 kg ice and 1 L of water, stirred for 15 min to complete the reaction and extracted with ethyl acetate (1 L×3). The combined organic layers were dried over sodium sulphate and evaporated to give the crude product (90 g, 97%) as a rust-colored solid, which was used for the next step without further purification; LC/MS: MS (ES$^+$) m/e 232 [M+H]+; $^1$H NMR (300 MHz, DMSO-d$_6$) δ ppm 5.48 (s, 2H), 6.07 (s, 2H), 7.39 (d, J=2.7 Hz, 1H), 7.64 (d, J=2.7 Hz, 1H).

b) 4-bromo-2-methyl-6-nitro-1H-benzo[d]imidazole

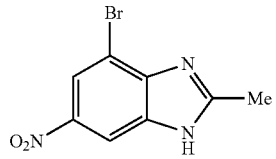 [SMILES: Cc1nc2c(Br)cc([N+](=O)[O-])cc2[nH]1]

A mixture of 3-bromo-5-nitrobenzene-1,2-diamine (90 g, 389 mmol) in acetic acid (800 mL) was stirred under reflux for 18 h. The solvent was removed in vacuo. The residue was purified by silica gel column chromatography (petroleum ether/ethyl acetate=1/1) to give the product (56 g, 56.6%) as a brown solid; LC/MS: MS (ES$^+$) m/e 256 [M+H]+; $^1$H NMR (300 MHz, DMSO-d$_6$) δ ppm 2.60 (s, 3H), 8.20 (d, J=1.8 Hz, 3H), 8.34 (d, J=1.8 Hz, 2H), 13.25 (s, br, 1H).

c) 7-bromo-2-methyl-3H-benzo[d]imidazol-5-amine

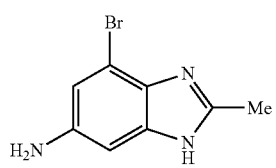

To a solution of 4-bromo-2-methyl-6-nitro-1H-benzo[d]imidazole (35 g, 137 mmol) and Tin(II) chloride dihydrate (185 g, 822 mmol) in methanol (800 mL) was added conc. HCl (10 mL), and the mixture was stirred at 65° C. for 2 h. Then the solvent was removed in vacuo, and the residue was diluted with 1N Na$_2$CO$_3$ solution (600 mL) and extracted with ethyl acetate (500 mL×3). The combined organic layers were washed with brine, dried over sodium sulphate and evaporated to give the crude product (30.2 g, 97%) as a brown solid; LC/MS: MS (ES$^+$) m/e 226 [M+H]+; $^1$H NMR (300 MHz, DMSO-d$_6$) δ ppm 2.38 (s, 3H), 4.98 (s, 2H), 6.52 (d, J=1.5 Hz, 1H), 6.66 (d, J=1.5 Hz, 1H), 11.86 (s, br, 1H).

d) 4-(4-bromo-2-methyl-1H-benzo[d]imidazol-6-yl)morpholine

A mixture of 7-bromo-2-methyl-3H-benzo[d]imidazol-5-amine (25 g, 111 mmol), 1-bromo-2-(2-bromoethoxy)ethane (38 g, 166 mmol) and DIPEA (21 g, 166 mmol) in ethylene glycol (600 mL) was stirred at 100° C. for 20 h. It was cooled to rt, and diluted with water (200 mL) and extracted with DCM (300 mL×4). The combined organic layers were washed with brine, dried over sodium sulphate and evaporated. The residue was purified by column chromatography (eluted with petroleum ether/ethyl acetate=1/1) to give the product (19 g, 58%) as a yellow solid; LC/MS: MS (ES$^+$) m/e 296 [M+H]+; $^1$H NMR (300 MHz, DMSO-d$_6$) δ ppm 2.44 (s, 3H), 3.07 (t, J=4.8 Hz, 4H), 3.74 (t, J=4.8 Hz, 4H), 6.85 (d, J=2.1 Hz, 1H), 7.04 (d, J=2.1 Hz, 1H), 12.20 (s, 1H).

Example 2

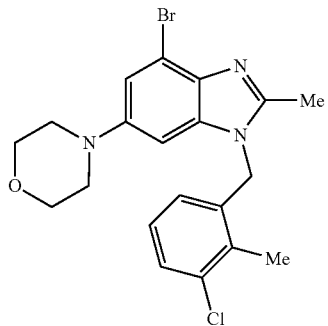 [SMILES: Cc1c(Cl)cccc1Cn1c(C)nc2c(Br)cc(N3CCOCC3)cc21]

Preparation of 4-(4-bromo-1-(3-chloro-2-methylbenzyl)-2-methyl-1H-benzo[d]imidazol-6-yl)morpholine a) 4-bromo-1-(3-chloro-2-methylbenzyl)-2-methyl-6-nitro-1H-benzo[d]imidazole

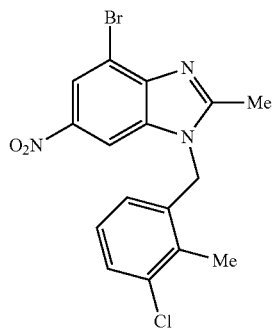

A mixture of 4-bromo-2-methyl-6-nitro-1H-benzo[d]imidazole (67 g, 258 mmol), 1-(bromomethyl)-3-chloro-2-methylbenzene (68 g, 309 mmol), prepared as described in example 1, step b, and cesium carbonate (126 g, 387 mmol) in DMF (800 mL) was stirred at 80° C. for 2 h. After cooled to room temperature, the mixture was poured into 1.5 L of water. The resulting precipitate was filtered, washed with water (300 mL), ether (100 mL) and dried in vacuo to give the crude product (100 g, 98%) as a brown solid; LC/MS: MS (ES$^+$) m/e 394 [M+H]+; $^1$H NMR (300 MHz, DMSO-d$_6$) δ ppm 2.48 (s, 3H), 2.54 (s, 3H), 5.73 (s, 2H), 6.06 (d, J=7.8 Hz, 1H), 7.06 (t, J=7.8 Hz, 1H), 7.38 (d, J=7.8 Hz, 1H), 8.30 (d, J=1.8 Hz, 1H), 8.60 (d, J=1.8 Hz, 1H).

b) 7-bromo-3-(3-chloro-2-methylbenzyl)-2-methyl-3H-benzo[d]imidazol-5-amine

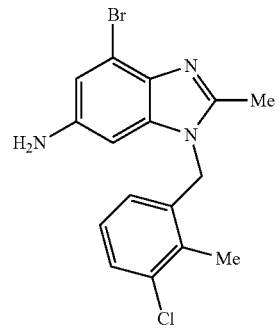 [SMILES: Cc1c(Cl)cccc1Cn1c(C)nc2c(Br)cc([N+](=O)[O-])cc21]

To a solution of 4-bromo-2-methyl-6-nitro-1H-benzo[d]imidazole (100 g, 253 mmol) and Tin (II) chloride dihydrate (342 g, 1.52 mol) in methanol (1.5 L) was added conc.HCl (50 mL), and the mixture was stirred at 70° C. for 3 h. Then the solvent was removed in vacuo, and the residue was diluted with 1N K$_2$CO$_3$ solution (1.5 L) and extracted with ethyl acetate (2 L×5). The combined organic layers were washed with brine, dried over sodium sulphate and evaporated to give the crude product (85 g, 87%) as a brown solid; LC/MS: MS (ES$^+$) m/e 366 [M+H]+; $^1$H NMR (300 MHz, DMSO-d$_6$) δ ppm 2.37 (s, 3H), 2.45 (s, 3H), 5.05 (s, 2H), 5.34 (s, 2H), 6.11 (d, J=8.1 Hz, 1H), 6.34 (d, J=1.5 Hz, 1H), 6.73 (d, J=1.5 Hz, 1H), 7.07 (t, J=8.1 Hz, 1H), 7.34 (d, J=8.1 Hz, 1H).

c) 4-(7-bromo-3-(3-chloro-2-methylbenzyl)-2-methyl-3H-benzo[d]imidazol-5-yl)morpholine A mixture of 7-bromo-3-(3-chloro-2-methylbenzyl)-2-methyl-3H-benzo[d]imidazol-5-amine (85 g, 233 mmol), 1-bromo-2-(2-bromoethoxy)ethane (108 g, 466 mmol) and DIPEA (60 g, 466 mmol) in ethylene glycol (1 L) was stirred at 100° C. for 18 h. It was cooled to rt, and diluted with water (1 L) and extracted with DCM (500 mL×4). The combined organic layers were washed with brine, dried over sodium sulphate and evaporated. The residue was purified by column chromatography (eluted with petroleum ether/ethyl acetate=1/1) to give the product (48 g, 47.5%) as a yellow solid; LC/MS: MS (ES$^+$) m/e 434 [M+H]+; $^1$H NMR (300 MHz, DMSO-d$_6$) δ ppm 2.36 (s, 3H), 2.46 (s, 3H), 3.04-3.07 (m, 4H), 3.68-3.72 (m, 4H), 5.47 (s, 2H), 6.04 (d, J=8.1 Hz, 1H), 6.96 (d, J=2.1 Hz, 1H), 7.06 (t, J=8.1 Hz, 1H), 7.09 (d, J=2.1 Hz, 1H), 7.35 (d, J=8.1 Hz, 1H).

Example 3

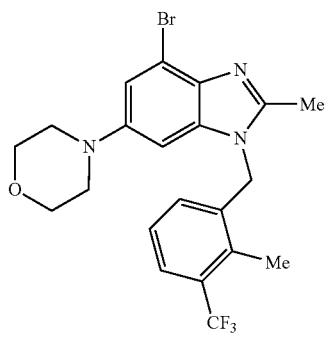 [SMILES: Cc1c(Cn2c(C)nc3c(Br)cc(N4CCOCC4)cc32)cccc1C(F)(F)F]

Preparation of 4-(4-bromo-2-methyl-1-(2-methyl-3-(trifluoromethyl)benzyl)-1H-benzo[d]imidazol-6-yl)morpholine a) 4-bromo-2-methyl-1-(2-methyl-3-(trifluoromethyl)benzyl)-6-nitro-1H-benzo[d]imidazole

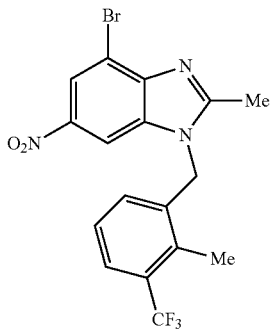

A mixture of 4-bromo-2-methyl-6-nitro-1H-benzo[d]imidazole (22 g, 78 mmol), prepared as described in example 1, step b, 1-(bromomethyl)-2-methyl-3-(trifluoromethyl)benzene (22 g, 86 mmol) and cesium carbonate (38 g, 117 mmol) in DMF (400 mL) was stirred at 80° C. for 3 h. After cooled to room temperature, the mixture was poured into 300 mL of water and extracted with ethyl acetate (200 mL×3). The combined organic layers were washed with brine, dried over sodium sulphate and combined with a separate batch prepared similarly and then evaporated to give the crude product (55 g, 62%) as a yellow solid; LC/MS: MS (ES$^+$) m/e 428 [M+H]+; $^1$H NMR (300 MHz, DMSO-d$_6$) δ ppm 2.54 (s, 3H), 2.55 (s, 3H), 5.78 (s, 2H), 6.35 (d, J=7.8 Hz, 1H), 7.25 (t, J=7.8 Hz, 1H), 7.63 (d, J=7.8 Hz, 1H), 8.31 (d, J=1.5 Hz, 1H), 8.63 (d, J=1.5 Hz, 1H).

b) 4-bromo-2-methyl-1-(2-methyl-3-(trifluoromethyl)benzyl)-1H-benzo[d]imidazol-6-amine

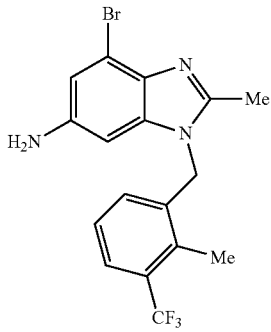 [SMILES: Cc1c(Cn2c(C)nc3c(Br)cc([N+](=O)[O-])cc32)cccc1C(F)(F)F]

To a solution of 4-bromo-2-methyl-1-(2-methyl-3-(trifluoromethyl)benzyl)-6-nitro-1H-benzo[d]imidazole (55 g, 129 mmol) in methanol (600 mL) was added conc. HCl (20 mL), SnCl$_2$ (174 g, 771 mmol) and the mixture was stirred at 70° C. for 2 h. Then the solvent was removed in vacuo, and the residue was diluted with 1N Na$_2$CO$_3$ solution (1.5 L) and extracted with DCM (200 mL×5). The combined organic layers were washed with brine, dried over sodium sulphate and evaporated to give the crude product (45 g, 88%) as a white solid; LC/MS: MS (ES$^+$) m/e 398 [M+H]+; $^1$H NMR (300 MHz, DMSO-d$_6$) δ ppm 2.37 (s, 3H), 2.52 (s, 3H), 5.06 (s, 2H), 5.40 (s, 2H), 6.35 (d, J=1.8 Hz, 1H), 6.37 (d, J=7.8 Hz, 1H), 6.74 (d, J=1.8 Hz, 1H), 7.26 (t, J=7.8 Hz, 1H), 7.60 (d, J=7.8 Hz, 1H).

c) 4-(7-bromo-2-methyl-3-(2-methyl-3-(trifluoromethyl)benzyl)-3H-benzo[d]imidazol-5-yl)morpholine A mixture of 7-bromo-2-methyl-3-(2-methyl-3-(trifluoromethyl)benzyl)-3H-benzo[d]imidazol-5-amine (45 g, 113 mmol), 1-bromo-2-(2-bromoethoxy)ethane (39 g, 169 mmol) and DIPEA (21 g, 169 mmol) in ethylene glycol (700 mL) was stirred at 100° C. for 20 h. It was cooled to rt, and diluted with water (300 mL) and extracted with DCM (300 mL×4). The combined organic layers were washed with brine, dried over sodium sulphate and evaporated. The residue was combined with previous batch prepared similarly and purified by column chromatography (eluted with petroleum ether/ethyl acetate=1/1) to give the product (42 g, 55%) as a yellow solid; LC/MS: MS (ES$^+$) m/e 468 [M+H]+; $^1$H NMR (300 MHz, DMSO-d$_6$) δ ppm 2.36 (s, 3H), 2.53 (s, 3H), 3.06 (t, J=4.5 Hz, 4H), 3.70 (t, J=4.5 Hz, 4H), 5.53 (s, 2H), 6.32 (d, J=7.8 Hz, 1H), 6.99 (d, J=1.5 Hz, 1H), 7.10 (d, J=1.5 Hz, 1H), 7.25 (t, J=7.8 Hz, 1H), 7.61 (d, J=7.8 Hz, 1H).

Example 4

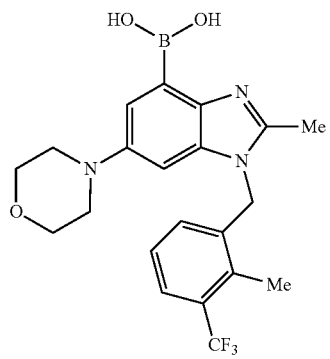 [SMILES: Cc1c(Cn2c(C)nc3c(B(O)O)cc(N4CCOCC4)cc32)cccc1C(F)(F)F]

Preparation of (2-methyl-1-(2-methyl-3-(trifluoromethyl)benzyl)-6-morpholino-1H-benzo[d]imidazol-4-yl)boronic acid Method B:

A mixture of 4-bromo-2-methyl-1-{[2-methyl-3-(trifluoromethyl)phenyl]methyl}-6-(4-morpholinyl)-1H-benzimidazole (600 mg, 1.281 mmol), Pd$_2$(dba)$_3$ (58.7 mg, 0.064 mmol), potassium acetate (377 mg, 3.84 mmol), XPhos (61.1 mg, 0.128 mmol) and bis(pinacolato)diboron (976 mg, 3.84 mmol) in 1,4-Dioxane (5 mL) was irradiated in a microwave reactor for 1 h at 120° C. The mixture was poured in water containing 1N HCl (pH 3-4) and extracted with EtOAc. The extracts were left stand overnight and a precipitate formed, which was collected, washed with EtOAc and dried to afford 390 mg of a mixture the desired material and traces of the des-bromo derivative. The reaction was repeated on another aliquot of 4-bromo-2-methyl-1-{[2-methyl-3-(trifluoromethyl)phenyl]methyl}-6-(4-morpholinyl)-1H-benzimidazole (600 mg, 1.281 mmol) with $Pd_2(dba)_3$ (58.7 mg, 0.064 mmol), potassium acetate (377 mg, 3.84 mmol), XPhos (61.1 mg, 0.128 mmol) and bis(pinacolato)diboron (976 mg, 3.84 mmol) in 1,4-Dioxane (5 mL). The mixture was irradiated in a microwave reactor for 1 h at 120° C., then poured in water/1N HCl (pH 3-4) and extracted with EtOAc. The extracts were left stand under a $N_2$ stream until a precipitate formed, which was collected, washed with EtOAc and dried to afford 360 mg of a mixture containing desired product and 2-3% of the des-bromo compound (2-3%). The two precipitates above were combined (750 mg total, HCl salt) and purified by RP-HPLC (Luna C18(2), 5 u, 30×250 mm, 60:40-300 mM aqueous ammonium trifluoroacetate (pH 2.4):Acetonitrile) in two batches (51 mg, single injection, main fraction was concentrated to ~40 ml. The pH was adjusted to 7.4 with conc. $NH_4OH$, and, after the addition of solid NaCl, the aqueous suspension was extracted with $CH_2Cl_2$ (3×20 mL). The combined extracts were dried over $Na_2SO_4$, concentrated to dryness to give 32 mg white of the desired product as a white solid. The remaining of the material was purified as above to give 427 mg of the desired product as a white solid. The two batches were analyzed, then combined to give (2-methyl-1-(2-methyl-3-(trifluoromethyl)benzyl)-6-morpholino-1H-benzo[d]imidazol-4-yl)boronic acid (435 mg, 0.984 mmol, 38.4% yield). MS ($ES^+$) m/e 434 [M+H]+; $^1$H NMR (400 MHz, DMSO-$d_6$, plus one drop of d-TFA) δ ppm 7.77 (d, J=2.02 Hz, 1H), 7.65 (d, J=7.83 Hz, 1H), 7.30 (d, J=2.02 Hz, 1H), 7.26 (t, J=8.08 Hz, 1H), 6.62 (d, J=8.08 Hz, 1H), 5.76 (s, 2H), 3.64-3.84 (m, 4H), 3.09-3.23 (m, 4H), 2.72 (s, 3H), 2.55 (s, 3H).

Example 5

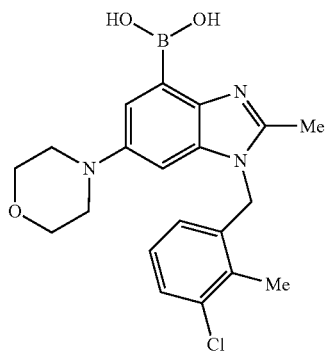 [SMILES: Cc1c(Cl)cccc1Cn1c(C)nc2c(B(O)O)cc(N3CCOCC3)cc21]

Preparation of (1-(3-chloro-2-methylbenzyl)-2-methyl-6-morpholino-1H-benzo[d]imidazol-4-yl)boronic acid Method B:

A mixture of 4-bromo-1-[(3-chloro-2-methylphenyl)methyl]-2-methyl-6-(4-morpholinyl)-1H-benzimidazole (200 mg, 0.460 mmol), $PdCl_2(dppf)$-$CH_2Cl_2$ adduct (18.78 mg, 0.023 mmol), bis(pinacolato)diboron (129 mg, 0.506 mmol) and potassium acetate (135 mg, 1.380 mmol) in 1,4-Dioxane (2 ml) was irradiated in a microwave reactor for 2 h at 140° C. The reaction looked incomplete by LC/MS and it was irradiated for additional 90 min at 140° C., then it was poured into water and extracted with EtOAc. The organic phase was washed with brine, dried over $Na_2SO_4$ and evaporated. The residue was purified on ISCO combiflash using a C-18 column and 25-65% Acetonitrile in water plus 0.1% TFA as eluent to give the desired product as a slightly grey powder containing 25-30% of the des-bromo derivative. The mixture (about 78 mg) was further purified on chiral phase (Chiralpak AD-H 30×250 mm, 80:20:0.1 Heptane:ETOH:Isopropylamine). The fraction containing product was concentrated to dryness, azeotroped with Acetonitrile (3×), and pumped under high vacuum at 50° C. for 30 min. to give [1-[(3-chloro-2-methylphenyl)methyl]-2-methyl-6-(4-morpholinyl)-1H-benzimidazol-4-yl]boronic acid (48.5 mg, 0.116 mmol, 25.3% yield) as a white powder. LC/MS: MS ($ES^+$) m/e 400 [M+H]+. $^1$H NMR (400 MHz, DMSO-$d_6$, plus 1 drop d-TFA) δ ppm 7.76 (d, J=2.02 Hz, 1H), 7.41 (d, J=8.08 Hz, 1H), 7.28 (d, J=2.02 Hz, 1H), 7.09 (t, J=7.96 Hz, 1H), 6.32 (d, J=7.83 Hz, 1H), 5.72 (s, 2H), 3.67-3.83 (m, 4H), 3.09-3.23 (m, 4H), 2.72 (s, 3H), 2.48 (s, 3H).

The title compound was also obtained following the procedure below:

Method A:

4-bromo-1-[(3-chloro-2-methylphenyl)methyl]-2-methyl-6-(4-morpholinyl)-1H-benzimidazole (7 g, 16.10 mmol) was suspended in Tetrahydrofuran (THF) (285 mL) and the mixture was stirred for 20 min, until a solution was obtained. The mixture was cooled to −78° C. and BuLi (14 mL, 35.0 mmol) was added dropwise. The mixture was stirred for few minutes, and then trimethyl borate (5 mL, 44.7 mmol) was added. The cold bath was removed and stirring was continued at rt overnight, then 6 N HCl (20 mL) was added and the solvent was evaporated under reduced pressure without heating. The residue was diluted with water and the pH was adjusted to 6-7 by the addition of 5 N NaOH. The solid formed was collected by filtration, washed with water and dried to give 7.25 g of crude.

Several batches were prepared, using additional 77 g of 4-bromo-1-[(3-chloro-2-methylphenyl)methyl]-2-methyl-6-(4-morpholinyl)-1H-benzimidazole (177.11 mmol), either by the method above or by using 2-isopropoxy-4,4,5,5-tetramethyl-1,3,2-dioxaborolane as the quenching agent. After standard work up the batches were combined with the above material and purified first by RP-HPLC (Luna C18(2), 5 u, 101×250 mm, 55:45 300 mM Aqueous ammonium trifluoroacetate (pH 2.8):acetonitrile), followed by purification on chiral phase (Chiralpak AD 101×250 mm, 20 u, 80:20 Heptane/EtOH plus 2% $HCO_2H$ and 1% Isopropylamine) and recrystallization from EtOAc to give [1-[(3-chloro-2-methylphenyl)methyl]-2-methyl-6-(4-morpholinyl)-1H-benzimidazol-4-yl]boronic acid (18.03 g, 45.17 mmol, 23.4% yield) as a beige powder.

Example 6

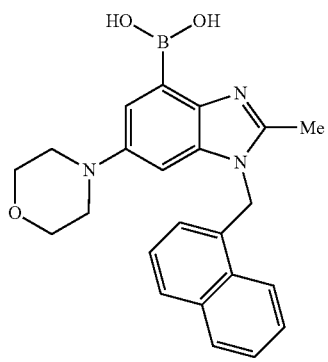 [SMILES: Cc1nc2c(B(O)O)cc(N3CCOCC3)cc2n1Cc1cccc2ccccc12]

Preparation of (2-methyl-6-morpholino-1-(naphthalen-1-ylmethyl)-1H-benzo[d]imidazol-4-yl)boronic acid a) 4-(4-bromo-2-methyl-1-(naphthalen-1-ylmethyl)-1H-benzo[d]imidazol-6-yl)morpholine

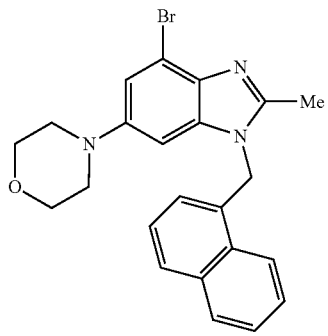 [SMILES: Cc1nc2c(Br)cc(N3CCOCC3)cc2n1Cc1cccc2ccccc12]

To a mixture of 4-(4-bromo-2-methyl-1H-benzo[d]imidazol-6-yl)morpholine (0.5 g, 1.688 mmol), prepared as described in example 1, in N,N-Dimethylformamide (DMF) (10 mL) was added 1-(bromomethyl)naphthalene (0.448 g, 2.026 mmol) and potassium carbonate (0.700 g, 5.06 mmol). The resulting reaction mixture was stirred at 80° C. for 4 h. It was cooled to room temperature and poured into water (100 mL). The aqueous mixture was extracted with DCM (100 mL×2). The combined organic phases were washed with Brine (100 mL) and concentrated. The crude material was purified on silica column (20~90% EtOAc in Hexane) to give the product as solid (0.53 g, 72%). $^1$H NMR (400 MHz, CHLOROFORM-d) δ ppm 2.57 (s, 3H) 2.97-3.13 (m, 4H) 3.61-3.89 (m, 4H) 5.76 (s, 2H) 6.53 (dd, J=7.07, 1.01 Hz, 1H) 6.56 (d, J=2.02 Hz, 1H) 7.17 (d, J=2.02 Hz, 1H) 7.32 (m, 1H) 7.58-7.73 (m, 2H) 7.83 (m, 1H) 7.98 (m, 1H) 8.08 (d, J=8.06 Hz, 1H); MS (ES+) m/e 436.1 [M+H]$^+$.

b) (2-methyl-6-morpholino-1-(naphthalen-1-ylmethyl)-1H-benzo[d]imidazol-4-yl)boronic acid The titled compound was prepared from 4-(4-bromo-2-methyl-1-(naphthalen-1-ylmethyl)-1H-benzo[d]imidazol-6-yl)morpholine (0.28 g, 0.642 mmol) using Method B to give the product (0.28 g, 52%). $^1$H NMR (400 MHz, DMSO-d$_6$) δ ppm 2.76 (s, 3H) 2.97-3.24 (m, 4H) 3.55-3.81 (m, 4H) 6.25 (s, 2H) 6.59 (d, J=7.07 Hz, 1H) 7.25-7.42 (m, 2H) 7.57-7.80 (m, 3H) 7.90 (d, J=8.34 Hz, 1H) 8.03 (d, J=7.83 Hz, 1H) 8.20 (d, J=8.49 Hz, 1H); MS (ES+) m/z 402.0 [M+H]$^+$.

Example 7

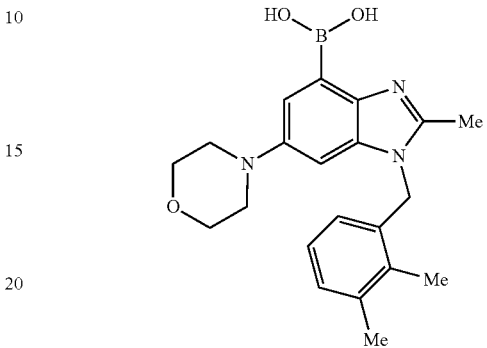

Preparation of (1-(2,3-dimethylbenzyl)-2-methyl-6-morpholino-1H-benzo[d]imidazol-4-yl)boronic acid a) 4-(4-bromo-1-(2,3-dimethylbenzyl)-2-methyl-1H-benzo[d]imidazol-6-yl)morpholine

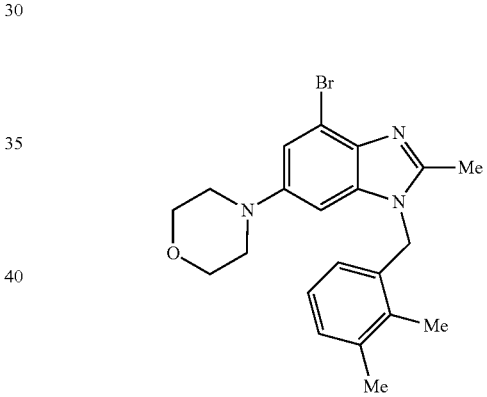

To the mixture of 4-(4-bromo-2-methyl-1H-benzo[d]imidazol-6-yl)morpholine (0.4 g, 1.351 mmol) in N,N-Dimethylformamide (DMF) (10 mL) was added 1-(bromomethyl)-2,3-dimethylbenzene (0.323 g, 1.621 mmol) and potassium carbonate (0.560 g, 4.05 mmol). The resulting reaction mixture was stirred at 80° C. for 3 h. It was cooled to room temperature and poured into water (100 mL). The aqueous mixture was extracted with DCM (100 mL×2). The combined organic phases were washed with Brine (100 mL) and concentrated. The crude material was purified on silica column (20~90% EtOAc in Hexane) to give the product as solid (0.4 g, 71%). $^1$H NMR (400 MHz, CHLOROFORM-d) δ ppm 2.33 (s, 3H) 2.37 (s, 3H) 2.53 (s, 3H) 2.98-3.14 (m, 4H) 3.66-3.93 (m, 4H) 5.24 (s, 2H) 6.24 (d, J=7.58 Hz, 1H) 6.53 (d, J=2.27 Hz, 1H) 6.89-7.00 (m, 1H) 7.06-7.17 (m, 2H); MS (ES+) m/e 414.1 [M+H]$^+$ b) (1-(2,3-dimethylbenzyl)-2-methyl-6-morpholino-1H-benzo[d]imidazol-4-yl)boronic acid The titled compound was prepared from 4-(4-bromo-1-(2,3-dimethylbenzyl)-2-methyl-1H-benzo[d]imidazol-6-yl)

morpholine (0.4 g, 0.965 mmol) using Method B to give the product (83 mg, 22%). $^1$H NMR (400 MHz, DMSO-$d_6$) δ ppm 2.30 (s, 6H) 2.71 (s, 3H) 3.09-3.20 (m, 4H) 3.69-3.79 (m, 4H) 5.69 (s, 2H) 6.18 (d, J=7.58 Hz, 1H) 6.96 (t, J=7.58 Hz, 1H) 7.13 (d, J=7.33 Hz, 1H) 7.29 (d, J=2.02 Hz, 1H) 7.77 (d, 1H); MS (ES+) m/z 380.3 [M+H]$^+$ Example 8

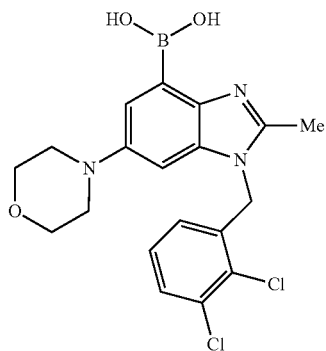 [SMILES: Cc1nc2c(B(O)O)cc(N3CCOCC3)cc2n1Cc1cccc(Cl)c1Cl]

Preparation of (1-(2,3-dichlorobenzyl)-2-methyl-6-morpholino-1H-benzo[d]imidazol-4-yl)boronic acid a) 4-(4-bromo-1-(2,3-dichlorobenzyl)-2-methyl-1H-benzo[d]imidazol-6-yl)morpholine

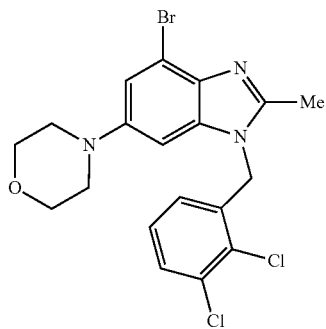 [SMILES: Cc1nc2c(Br)cc(N3CCOCC3)cc2n1Cc1cccc(Cl)c1Cl]

To the mixture of 4-(4-bromo-2-methyl-1H-benzo[d]imidazol-6-yl)morpholine (0.8 g, 2.70 mmol) in N,N-Dimethylformamide (DMF) (10 mL) was added 1-(bromomethyl)-2,3-dichlorobenzene (0.778 g, 3.24 mmol) and potassium carbonate (1.120 g, 8.10 mmol). The resulting reaction mixture was stirred at 90° C. for 4 h. It was cooled to room temperature and poured into water (100 mL). The aqueous mixture was extracted with DCM (100 mL×2). The combined organic phases were washed with Brine (100 mL) and concentrated. The crude material was purified on silica column (20~90% EtOAc in Hexane) to give the product as solid (1.01 g, 82%). $^1$H NMR (400 MHz, CHLOROFORM-d) δ ppm 2.55 (s, 3H) 3.03-3.18 (m, 4H) 3.79-3.89 (m, 4H) 5.35 (s, 2H) 6.31 (dd, J=7.83, 1.26 Hz, 1H) 6.54 (d, J=2.02 Hz, 1H) 7.08 (t, J=7.96 Hz, 1H) 7.17 (d, J=2.02 Hz, 1H) 7.45 (dd, J=8.06, 1.55 Hz, 1H); MS (ES+) m/e 453.8 [M+H]$^+$.

b) (1-(2,3-dichlorobenzyl)-2-methyl-6-morpholino-1H-benzo[d]imidazol-4-yl)boronic acid The titled compound was prepared from 4-(4-bromo-1-(2,3-dichlorobenzyl)-2-methyl-1H-benzo[d]imidazol-6-yl) morpholine (0.9 g, 1.977 mmol) using Method A with trimethylborate to give the product (82 mg, 10%). $^1$H NMR (400 MHz, DMSO-$d_6$) δ ppm 2.45 (s, 3H) 2.97-3.12 (m, 4H) 3.69-3.77 (m, 4H) 5.57 (s, 2H) 6.32 (dd, J=7.83, 1.01 Hz, 1H) 7.12 (d, J=2.02 Hz, 1H) 7.26 (t, J=7.96 Hz, 1H) 7.36 (d, J=2.02 Hz, 1H) 7.61 (dd, J=8.08, 1.26 Hz, 1H) 8.66 (s, 2H); MS (ES+) m/z 420.1 [M+H]$^+$.

Example 9

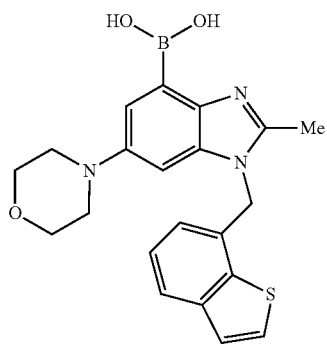 [SMILES: Cc1nc2c(B(O)O)cc(N3CCOCC3)cc2n1Cc1cccc2ccsc12]

Preparation of 4-(1-(benzo[b]thiophen-7-ylmethyl)-4-bromo-2-methyl-1H-benzo[d]imidazol-6-yl)morpholine a) 4-(1-(benzo[b]thiophen-7-ylmethyl)-4-bromo-2-methyl-1H-benzo[d]imidazol-6-yl)morpholine

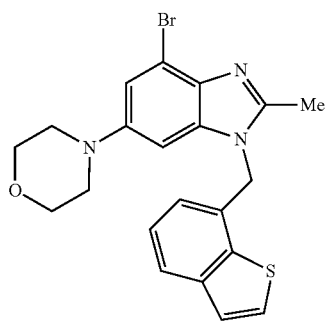 [SMILES: Cc1nc2c(Br)cc(N3CCOCC3)cc2n1Cc1cccc2ccsc12]

To the mixture of 4-(4-bromo-2-methyl-1H-benzo[d]imidazol-6-yl)morpholine (0.8 g, 2.70 mmol) in N,N-Dimethylformamide (DMF) (10 mL) was added 7-(bromomethyl)benzo[b]thiophene (0.920 g, 4.05 mmol)) and potassium carbonate (1.120 g, 8.10 mmol). The resulting reaction mixture was stirred at 90° C. for 2 h, then more 7-(bromomethyl)benzo[b]thiophene (0.920 g, 4.05 mmol) was added in and the reaction mixture was stirred at 100° C. for 4 h. It was cooled to room temperature and poured into water (100 mL). The aqueous mixture was extracted with DCM (100 mL×2). The combined organic phase was washed with Brine (100 mL) and concentrated. The crude material was purified on silica column (20~90% EtOAc in Hexane) to give the product as solid (0.69 g, 58% %). $^1$H NMR (400 MHz, DMSO-$d_6$) δ ppm 2.42 (s, 3H) 2.95-3.07 (m, 4H) 3.66-3.72 (m, 4H) 5.69 (s, 2H) 6.81 (d, J=7.07 Hz, 1H) 7.00 (d, J=2.02 Hz, 1H) 7.09 (d, J=2.02 Hz, 1H) 7.36 (t, J=7.58 Hz, 1H) 7.53 (d, J=5.56 Hz, 1H) 7.79 (d, J=5.56 Hz, 1H) 7.85 (d, J=7.65 Hz, 1H); MS (ES+) m/e 442.0 [M+H]+.

b) 4-(1-(benzo[b]thiophen-7-ylmethyl)-4-bromo-2-methyl-1H-benzo[d]imidazol-6-yl)morpholine The titled compound was prepared from 4-(1-(benzo[b]thiophen-7-ylmethyl)-4-bromo-2-methyl-1H-benzo[d]imidazol-6-yl)morpholine (0.34 g, 0.769 mmol) using Method B to give the product (0.242 g, 37%). ¹H NMR (400 MHz, DMSO-d₆) δ ppm 2.78 (s, 3H) 3.04-3.24 (m, 4H) 3.51-3.83 (m, 4H) 5.97 (s, 2H) 7.06 (d, J=7.33 Hz, 1H) 7.26-7.46 (m, 2H) 7.55 (d, J=5.31 Hz, 1H) 7.71-7.84 (m, 2H) 7.90 (d, J=7.83 Hz, 1H); MS (ES+) m/z 408.1 [M+H]+.

Example 10

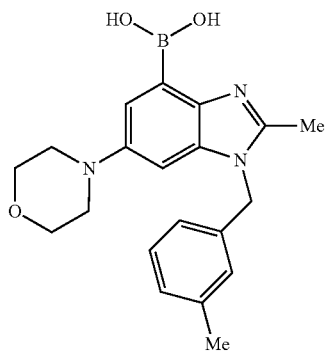 [SMILES: Cc1cccc(Cn2c(C)nc3c(B(O)O)cc(N4CCOCC4)cc32)c1]

Preparation of (2-methyl-1-(3-methylbenzyl)-6-morpholino-1H-benzo[d]imidazol-4-yl)boronic acid a) 4-(4-bromo-2-methyl-1-(3-methylbenzyl)-1H-benzo[d]imidazol-6-yl)morpholine

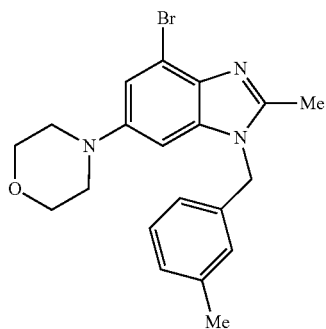

To the mixture of 4-(4-bromo-2-methyl-1H-benzo[d]imidazol-6-yl)morpholine (0.7 g, 2.364 mmol) in N,N-Dimethylformamide (DMF) (10 mL) was added 1-(bromomethyl)-3-methylbenzene (0.525 g, 2.84 mmol) and potassium carbonate (0.980 g, 7.09 mmol). The resulting reaction mixture was stirred at 90° C. for 4 h. It was cooled to room temperature and poured into water (100 mL). The aqueous mixture was extracted with DCM (100 mL×2). The combined organic phases were washed with Brine (100 mL) and concentrated. The crude material was purified on silica column (20~70% EtOAc in Hexane) to give the product as oil (0.686 g, 73%). ¹H NMR (400 MHz, CHLOROFORM-d) δ ppm 2.31 (s, 3H) 2.57 (s, 3H) 3.01-3.18 (m, 4H) 3.75-3.92 (m, 4H) 5.24 (s, 2H) 6.64 (d, J=2.02 Hz, 1H) 6.75-6.89 (m, 2H) 7.03-7.17 (m, 2H) 7.18-7.26 (m, 1H); MS (ES+) m/e 400.0 [M+H]+.

b) (2-methyl-1-(3-methylbenzyl)-6-morpholino-1H-benzo[d]imidazol-4-yl)boronic acid The titled compound was prepared from 4-(4-bromo-2-methyl-1-(3-methylbenzyl)-1H-benzo[d]imidazol-6-yl)morpholine (0.34 g, 0.849 mmol) using Method B to give the product (0.428 g, 66%). ¹H NMR (400 MHz, DMSO-d₆) δ ppm 2.25 (s, 3H) 2.82 (s, 3H) 3.14-3.38 (m, 4H) 3.71-3.91 (m, 4H) 5.63 (s, 2H) 7.03 (d, J=7.58 Hz, 1H) 7.07-7.16 (m, 2H) 7.20-7.27 (m, 1H) 7.45 (d, J=2.02 Hz, 1H) 7.79 (d, J=1.89 Hz, 1H); MS (ES+) m/z 366.1 [M+H]+.

Example 11

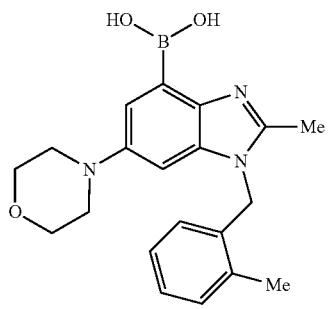 [SMILES: Cc1ccccc1Cn1c(C)nc2c(B(O)O)cc(N3CCOCC3)cc21]

Preparation of (2-methyl-1-(2-methylbenzyl)-6-morpholino-1H-benzo[d]imidazol-4-yl)boronic acid a) 4-(4-bromo-2-methyl-1-(2-methylbenzyl)-1H-benzo[d]imidazol-6-yl)morpholine

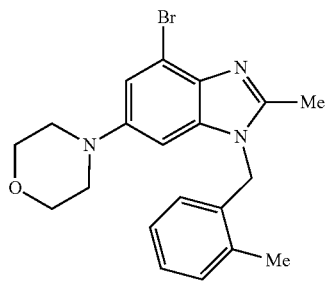 [SMILES: Cc1ccccc1Cn1c(C)nc2c(Br)cc(N3CCOCC3)cc21]

To the mixture of 4-(4-bromo-2-methyl-1H-benzo[d]imidazol-6-yl)morpholine (0.7 g, 2.364 mmol) in N,N-Dimethylformamide (DMF) (10 mL) was added in 1-(bromomethyl)-2-methylbenzene (0.525 g, 2.84 mmol) and potassium carbonate (0.980 g, 7.09 mmol). The resulting reaction mixture was stirred at 90° C. for 4 h. It was cooled to room temperature and poured into water (100 mL). The aqueous mixture was extracted with DCM (100 mL×2). The combined organic phases were washed with Brine (100 mL) and concentrated. The crude material was purified on silica column (20~90% EtOAc in Hexane) to give the product as solid (0.726 g, 77%). ¹H NMR (400 MHz, CHLOROFORM-d) δ ppm 2.43 (s, 3H) 2.54 (s, 3H) 3.00-3.14 (m, 4H) 3.78-3.90 (m, 4H) 5.22 (s, 2H) 6.44 (d, J=7.83 Hz, 1H) 6.53 (d, J=2.02 Hz, 1H) 7.02-7.12 (m, 1H) 7.15 (d, J=2.02 Hz, 1H) 7.18-7.27 (m, 2H); MS (ES+) m/e 400.0 [M+H]⁺.

b) (2-methyl-1-(2-methylbenzyl)-6-morpholino-1H-benzo[d]imidazol-4-yl)boronic acid The titled compound was prepared from 4-(4-bromo-2-methyl-1-(2-methylbenzyl)-1H-benzo[d]imidazol-6-yl)morpholine (0.36 g, 0.899 mmol) using Method B to give the product (0.458 g, 66%). ¹H NMR (400 MHz, DMSO-d₆) δ ppm 2.41 (s, 3H) 2.72 (s, 3H) 3.17-3.24 (m, 4H) 3.73-3.80 (m, 4H) 5.66 (s, 2H) 6.42 (d, J=7.58 Hz, 1H) 7.05 (t, J=7.33 Hz, 1H) 7.15-7.23 (m, 1H) 7.25-7.29 (m, 1H) 7.35 (d, J=2.02 Hz, 1H) 7.82 (d, J=2.21 Hz, 1H); MS (ES+) m/z 366.2 [M+H]⁺.

Example 12

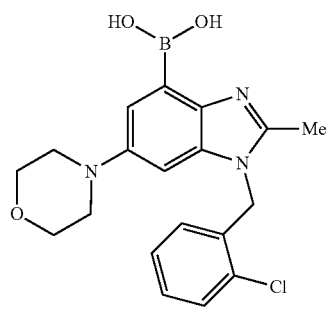 [SMILES: Cc1nc2c(B(O)O)cc(N3CCOCC3)cc2n1Cc1ccccc1Cl]

Preparation of (1-(2-chlorobenzyl)-2-methyl-6-morpholino-1H-benzo[d]imidazol-4-yl)boronic acid a) 4-(4-bromo-1-(2-chlorobenzyl)-2-methyl-1H-benzo[d]imidazol-6-yl)morpholine

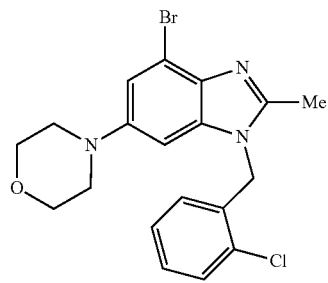 [SMILES: Cc1nc2c(Br)cc(N3CCOCC3)cc2n1Cc1ccccc1Cl]

To the mixture of 4-(4-bromo-2-methyl-1H-benzo[d]imidazol-6-yl)morpholine (0.8 g, 2.70 mmol) in N,N-Dimethylformamide (DMF) (10 mL) was added 1-(bromomethyl)-2-chlorobenzene (0.666 g, 3.24 mmol) and potassium carbonate (1.120 g, 8.10 mmol). The resulting reaction mixture was stirred at 90° C. for 4 h. It was cooled to room temperature and poured into water (100 mL). The aqueous mixture was extracted with DCM (100 mL×2). The combined organic phases were washed with Brine (100 mL) and concentrated. The crude material was purified on silica column (20~70% EtOAc in Hexane) to give the product as solid (0.96 g, 84%). ¹H NMR (400 MHz, CHLOROFORM-d) δ ppm 2.56 (s, 3H) 2.89-3.18 (m, 4H) 3.66-3.91 (m, 4H) 5.34 (s, 2H) 6.35-6.50 (m, 1H) 6.57 (d, J=2.27 Hz, 1H) 7.00-7.21 (m, 2H) 7.21-7.33 (m, 1H) 7.47 (dd, J=7.82 1.11 Hz, 1H); MS (ES+) m/e 420.0 [M+H]⁺.

b) (1-(2-chlorobenzyl)-2-methyl-6-morpholino-1H-benzo[d]imidazol-4-yl)boronic acid The titled compound was prepared from 4-(4-bromo-1-(2-chlorobenzyl)-2-methyl-1H-benzo[d]imidazol-6-yl)morpholine (0.2 g, 0.475 mmol) using Method A with trimethylborate to give the product (0.272 g, 39%). ¹H NMR (400 MHz, DMSO-d₆) δ ppm 2.77 (s, 3H) 3.15-3.25 (m, 4H) 3.65-3.82 (m, 4H) 5.75 (s, 2H) 6.82-6.88 (m, 1H) 7.22-7.30 (m, 1H) 7.32-7.40 (m, 2H) 7.56 (dd, J=7.96, 1.14 Hz, 1H) 7.80 (d, J=1.95 Hz, 1H); MS (ES+) 386.0 m/z Example 13

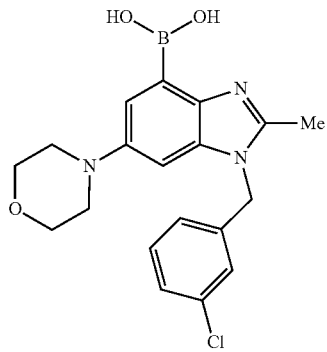 [SMILES: Cc1nc2c(B(O)O)cc(N3CCOCC3)cc2n1Cc1cccc(Cl)c1]

Preparation of (1-(3-chlorobenzyl)-2-methyl-6-morpholino-1H-benzo[d]imidazol-4-yl)boronic acid a) 4-(4-bromo-1-(3-chlorobenzyl)-2-methyl-1H-benzo[d]imidazol-6-yl)morpholine

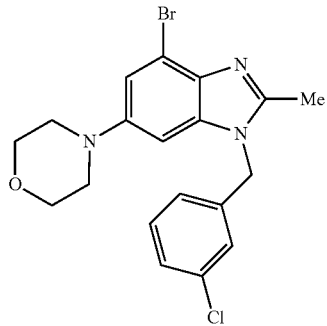 [SMILES: Cc1nc2c(Br)cc(N3CCOCC3)cc2n1Cc1cccc(Cl)c1]

To a mixture of 4-(4-bromo-2-methyl-1H-benzo[d]imidazol-6-yl)morpholine (0.7 g, 2.364 mmol) in N,N-Dimethylformamide (DMF) (10 mL) was added 1-(bromomethyl)-3-chlorobenzene (0.583 g, 2.84 mmol) and potassium carbonate (0.980 g, 7.09 mmol). The resulting reaction mixture was stirred at 90° C. for 4 h. It was cooled to room temperature and poured into water (100 mL). The aqueous mixture was extracted with DCM (100 mL×2). The combined organic phases were washed with Brine (100 mL) and concentrated. The crude material was purified on silica column (20~70% EtOAc in Hexane) to give the product as solid (0.65 g, 65%). $^1$H NMR (400 MHz, CHLOROFORM-d) δ ppm 2.57 (s, 3H) 2.90-3.16 (m, 4H) 3.69-3.95 (m, 4H) 5.25 (s, 2H) 6.60 (d, J=2.02 Hz, 1H) 6.88 (d, J=7.07 Hz, 1H) 7.07 (s, 1H) 7.16 (d, J=2.02 Hz, 1H) 7.20-7.37 (m, 2H); MS (ES+) m/e 420.0 [M+H]$^+$.

b) (1-(3-chlorobenzyl)-2-methyl-6-morpholino-1H-benzo[d]imidazol-4-yl)boronic acid The titled compound was prepared from 4-(4-bromo-1-(3-chlorobenzyl)-2-methyl-1H-benzo[d]imidazol-6-yl)morpholine (0.65 g, 1.545 mmol) using Method A with trimethylborate to give the product (109 mg, 17%). $^1$H NMR (400 MHz, DMSO-d$_6$) δ ppm 2.82 (s, 3H) 3.22 (m, 4H) 3.78 (m, 4H) 5.69 (s, 2H) 7.19 (m, 1H) 7.33-7.48 (m, 4H) 7.78 (s, 1H); MS (ES+) 386.0 m/z.

Example 14

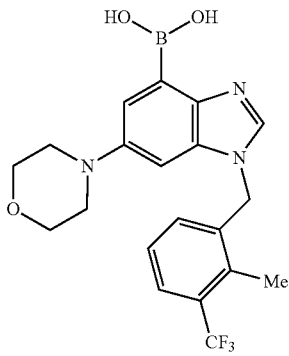 [SMILES: Cc1c(Cn2cnc3c(B(O)O)cc(N4CCOCC4)cc32)cccc1C(F)(F)F]

Preparation of (1-(2-methyl-3-(trifluoromethyl)benzyl)-6-morpholino-1H-benzo[d]imidazol-4-yl)boronic acid a) 4-bromo-6-nitro-1H-benzo[d]imidazole

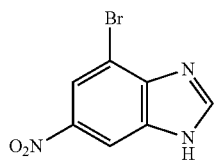 [SMILES: O=[N+]([O-])c1cc(Br)c2nc[nH]c2c1]

To a 100 mL round bottomed flask was added 3-bromo-5-nitrobenzene-1,2-diamine (5 g, 21.55 mmol) and formic acid (3.25 mL, 86 mmol) in Toluene (10 mL). The solution was heated to reflux overnight. The product precipitated and was triturated with toluene, diluted with water and adjusted to ph 9 with 6N NaOH. The solid was filtered, washed with water and placed in a vacuum oven overnight to yield 4-bromo-6-nitro-1H-benzo[d]imidazole (5.02 g, 20.74 mmol, 96% yield) as a brown solid. $^1$H NMR (400 MHz, DMSO-d$_6$) δ ppm 8.16 (s, 1H) 8.29 (d, J=2.02 Hz, 1H) 8.51 (d, J=2.02 Hz, 1H) 8.66 (s, 1H); LC/MS: MS (ES$^+$) m/e 243 [M+H]+.

b) 4-bromo-1-(2-methyl-3-(trifluoromethyl)benzyl)-6-nitro-1H-benzo[d]imidazole

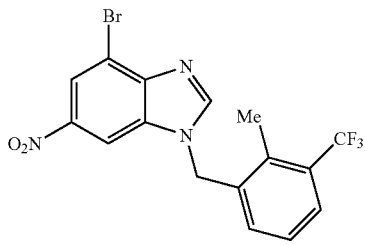 [SMILES: Cc1c(Cn2cnc3c(Br)cc([N+](=O)[O-])cc32)cccc1C(F)(F)F]

Into a 250 mL round bottomed flask charged with 4-bromo-6-nitro-1H-benzo[d]imidazole (5 g, 20.66 mmol) in N,N-Dimethylformamide (DMF) (100 mL) was added 1-(bromomethyl)-2-methyl-3-(trifluoromethyl)benzene (7.84 g, 31.0 mmol) and potassium carbonate (8.57 g, 62.0 mmol). The resulting reaction mixture was stirred 1 h at 60° C., cooled to room temperature and poured into water, extracted with ethyl acetate, washed with water, brine, dried (MgSO$_4$) and evaporated. The residue was purified on a silica gel cartridge and eluted with a gradient of 0% ethyl acetate/hexanes to 80% over 10 column volumes. The expected compound was collected and evaporated to yield 4-bromo-1-(2-methyl-3-(trifluoromethyl)benzyl)-6-nitro-1H-benzo[d]imidazole (2.58 g, 6.23 mmol, 30.2% yield) as a tan solid. $^1$H NMR (400 MHz, CHLOROFORM-d) δ ppm 2.47 (s, 3H) 5.52 (s, 2H) 7.02 (d, J=7.58 Hz, 1H) 7.27-7.37 (m, 1H) 7.72 (d, J=8.08 Hz, 1H) 8.12 (s, 1H) 8.25 (d, J=2.02 Hz, 1H) 8.48 (d, 1H); LC/MS: MS (ES$^+$) m/e 415 [M+H]+.

c) 4-bromo-1-(2-methyl-3-(trifluoromethyl)benzyl)-1H-benzo[d]imidazol-6-amine

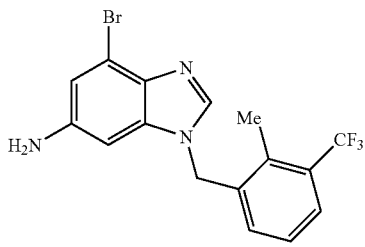

To a solution of 4-bromo-1-(2-methyl-3-(trifluoromethyl)benzyl)-6-nitro-1H-benzo[d]imidazole (2.5 g, 6.04 mmol) in Methanol (30 mL) in a 250 ml round bottomed flask was added Tin(II)chloride dihydrate (8.17 g, 36.2 mmol) and HCl (1.65 mL, 54.3 mmol). The reaction mixture was left to stir at 80° C. for 1 h. The solvent was removed and diluted with water (100 mL) and this solution was decanted into a 250 mL Erlenmeyer flask. The brown residue in the round bottomed flask was dissolved in 100 mL of EtOAc and washed with 1N NaOH, brine, dried and evaporated to yield a brown solid. The water layer was extracted with EtOAc, washed with 1N NaOH, brine, dried (MgSO$_4$) and evaporated to a brown solid. The solids found to be identical by 1 cms and were combined to yield 4-bromo-1-(2-methyl-3-(trifluoromethyl)benzyl)-1H-benzo[d]imidazol-6-amine (2.28 g, 5.93 mmol, 98% yield). $^1$H NMR (400 MHz, CHLOROFORM-d) δ ppm 2.44 (s, 3H) 5.24 (s, 2H) 6.39 (d, J=2.02 Hz, 1H) 6.87 (d, J=8.08 Hz, 1H) 6.92 (d, J=2.02 Hz, 1H) 7.21 (t, J=7.83 Hz, 1H) 7.62 (d, J=7.83 Hz, 1H) 7.69 (s, 1H); LC/MS: MS (ES$^+$) m/e 385 [M+H]+.

d) 4-(4-bromo-1-(2-methyl-3-(trifluoromethyl)benzyl)-1H-benzo[d]imidazol-6-yl)morpholine

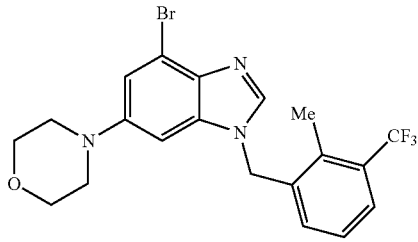 [SMILES: Cc1c(Cn2cnc3c(Br)cc(N4CCOCC4)cc32)cccc1C(F)(F)F]

Into a 100 ml round bottomed flask with 4-bromo-1-(2-methyl-3-(trifluoromethyl)benzyl)-1H-benzo[d]imidazol-6-amine (2.28 g, 5.93 mmol), tetrabutylammonium iodide (0.110 g, 0.297 mmol) was added 6N sodium hydroxide (14.84 ml, 89 mmol) and 1-bromo-2-(2-bromoethoxy)ethane (1.480 ml, 11.87 mmol). The reaction was heated to 110° C. for 2 h, cooled to room temperature and the mixture was extracted with EtOAc. The combined organic phase was washed with Brine (20 mL) and concentrated. The residue was purified on a silica gel cartridge and eluted with a gradient of 0% ethyl acetate/hexanes to 80% over 10 column volumes. The appropriate fractions were collected and evaporated to yield 4-(4-bromo-1-(2-methyl-3-(trifluoromethyl)benzyl)-1H-benzo[d]imidazol-6-yl)morpholine (508 mg, 1.118 mmol, 18.84% yield). $^1$H NMR (400 MHz, CHLOROFORM-d) δ ppm 2.40 (s, 3H) 3.00-3.09 (m, 4H) 3.76-3.81 (m, 4H) 5.26 (s, 2H) 6.54 (d, J=2.02 Hz, 1H) 6.85 (d, J=7.58 Hz, 1H) 7.13-7.21 (m, 2H) 7.57 (d, J=7.83 Hz, 1H) 7.68 (s, 1H); LC/MS: MS (ES$^+$) m/e 455 [M+H]+.

e) (1-(2-methyl-3-(trifluoromethyl)benzyl)-6-morpholino-1H-benzo[d]imidazol-4-yl)boronic acid The titled compound was prepared from 4-(4-bromo-1-(2-methyl-3-(trifluoromethyl)benzyl)-1H-benzo[d]imidazol-6-yl)morpholine (500 mg, 1.101 mmol) using Method B to give the product (45 mg, 0.107 mmol, 9.75% yield). $^1$H NMR (400 MHz, METHANOL-d$_4$) δ ppm 2.49-2.57 (m, 3H) 3.21-3.27 (m, 4H) 3.81-3.92 (m, 4H) 5.81-5.89 (m, 2H) 7.16-7.23 (m, 2H) 7.35-7.44 (m, 1H) 7.69-7.80 (m, 2H) 9.19 (none, 1H). LC/MS: MS (ES$^+$) m/e 420 [M+H]+.

Example 15

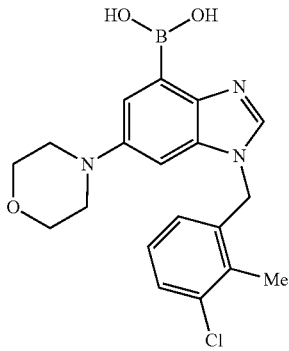 [SMILES: Cc1c(Cl)cccc1Cn1cnc2c(B(O)O)cc(N3CCOCC3)cc21]

Preparation of (1-(3-chloro-2-methylbenzyl)-6-morpholino-1H-benzo[d]imidazol-4-yl)boronic acid a) 4-bromo-1-(3-chloro-2-methylbenzyl)-6-nitro-1H-benzo[d]imidazole

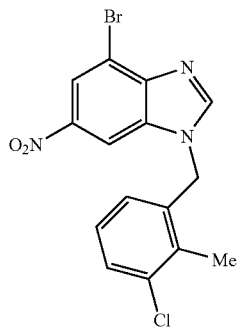 [SMILES: Cc1c(Cl)cccc1Cn1cnc2c(Br)cc([N+](=O)[O-])cc21]

Into a 250 mL round bottomed flask charged with 4-bromo-6-nitro-1H-benzo[d]imidazole (5 g, 20.66 mmol) in N,N-Dimethylformamide (DMF) (100 mL) was added 1-(bromomethyl)-3-chloro-2-methylbenzene (6.80 g, 31.0 mmol) and potassium carbonate (8.57 g, 62.0 mmol The resulting reaction mixture was stirred 1 h at 60° C., cooled to room temperature and poured into water, extracted with ethyl acetate, washed with water, brine, dried (MgSO$_4$) and evaporated. The residue was purified on a silica gel cartridge and eluted with a gradient of 0% ethyl acetate/hexanes to 80% over 10 column volumes. The expected compound was collected and evaporated to yield 4-bromo-1-(3-chloro-2-methylbenzyl)-6-nitro-1H-benzo[d]imidazole (3.05 g, 8.01 mmol, 38.8% yield) as a tan solid. $^1$H NMR (400 MHz, DMSO-d$_6$) δ ppm 2.40 (s, 3H) 5.79 (s, 2H) 6.61 (d, J=7.58 Hz, 1H) 7.16 (t, J=7.83 Hz, 1H) 7.42 (d, J=7.58 Hz, 1H) 8.34 (d, J=2.02 Hz, 1H) 8.65 (d, J=2.02 Hz, 1H) 8.73 (s, 1H); LC/MS: MS (ES$^+$) m/e 381 [M+H]+.

b) 4-bromo-1-(3-chloro-2-methylbenzyl)-1H-benzo[d]imidazol-6-amine

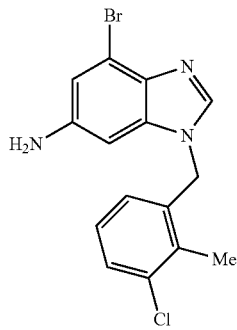

To a solution of 4-bromo-1-(3-chloro-2-methylbenzyl)-6-nitro-1H-benzo[d]imidazole (3.05 g, 8.01 mmol) in Methanol (35 mL) in a 250 ml round bottomed flask was added Tin(II)chloride dihydrate (10.85 g, 48.1 mmol) and HCl (2.19 mL, 72.1 mmol). The reaction mixture was left to stir at 80° C. for 1 h. The solvent was removed and diluted with water (100 mL) and this solution was decanted into a 250 mL Erlenmeyer flask. The brown residue in the round bottomed flask was dissolved in 100 mL of EtOAc and washed with 1N NaOH, brine, dried and evaporated to yield a brown solid. The water layer was extracted with EtOAc, washed with 1N NaOH, brine, dried (MgSO$_4$) and evaporated to a brown solid. The solids found to be identical by 1 cms and were combined to yield a brown solid 4-bromo-1-(3-chloro-2-methylbenzyl)-1H-benzo[d]imidazol-6-amine (2.33 g, 6.64 mmol, 83% yield). $^1$H NMR (400 MHz, DMSO-d$_6$) δ ppm 2.40 (s, 3H) 5.45 (s, 2H) 6.47 (d, J=1.52 Hz, 1H) 6.56 (d, J=7.58 Hz, 1H) 6.86 (d, J=1.52 Hz, 1H) 7.14 (s, 1H) 7.39 (d, J=7.83 Hz, 1H) 8.11 (s, 1H); LC/MS: MS (ES$^+$) m/e 351 [M+H]+.

c) 4-(4-bromo-1-(3-chloro-2-methylbenzyl)-1H-benzo[d]imidazol-6-yl)morpholine

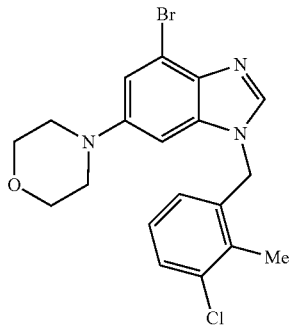 [SMILES: Cc1c(Cl)cccc1Cn1cnc2c(Br)cc(N3CCOCC3)cc21]

Into a 100 ml round bottomed flask with 4-bromo-1-(3-chloro-2-methylbenzyl)-1H-benzo[d]imidazol-6-amine (2.33 g, 6.64 mmol), tetrabutylammonium iodide (0.123 g, 0.332 mmol) was added 6N sodium hydroxide (16.61 ml, 100 mmol) and 1-bromo-2-(2-bromoethoxy)ethane (1.657 ml, 13.29 mmol). The reaction was heated to 110° C. for 2 h, cooled to room temperature and the mixture was extracted with EtOAc. The combined organic phase was washed with Brine (20 mL) and concentrated. The residue was purified by reversed phase HPLC and was eluted with a gradient of acetonitrile (0.1% TFA) and water (0.1% TFA v/v) (30-65%) over 12 minutes. The appropriate fractions were collected and evaporated to yield 4-(4-bromo-1-(3-chloro-2-methylbenzyl)-1H-benzo[d]imidazol-6-yl)morpholine (483 mg, 1.148 mmol, 17.28% yield). $^1$H NMR (400 MHz, CHLOROFORM-d) δ ppm 2.37 (s, 3H) 3.14-3.22 (m, 4H) 3.84-3.93 (m, 4H) 5.48 (s, 2H) 6.71 (d, J=2.02 Hz, 1H) 6.91 (d, J=7.58 Hz, 1H) 7.16 (t, J=7.83 Hz, 1H) 7.34 (d, J=2.02 Hz, 1H) 7.44 (d, J=7.58 Hz, 1H) 8.84 (br. s., 1H); LC/MS: MS (ES$^+$) m/e 421 [M+H]+.

d) (1-(3-chloro-2-methylbenzyl)-6-morpholino-1H-benzo[d]imidazol-4-yl)boronic acid The titled compound was prepared from 4-(4-bromo-1-(3-chloro-2-methylbenzyl)-1H-benzo[d]imidazol-6-yl)morpholine (400 mg, 0.951 mmol) using Method A with trimethylborate to give the product (23 mg, 6%). $^1$H NMR (400 MHz, METHANOL-d$_4$) δ ppm 2.41 (s, 3H) 3.12-3.18 (m, 4H) 3.82-3.90 (m, 4H) 5.61 (s, 2H) 6.89 (d, J=7.07 Hz, 2H) 7.17 (t, J=7.83 Hz, 1H) 7.27 (d, J=2.27 Hz, 1H) 7.42 (d, J=8.08 Hz, 1H) 8.39 (s, 1H); LC/MS: MS (ES$^+$) m/e 386 [M+H]+.

Example 16

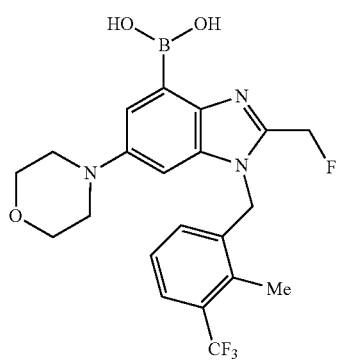 [SMILES: Cc1c(Cn2c(CF)nc3c(B(O)O)cc(N4CCOCC4)cc32)cccc1C(F)(F)F]

Preparation of (2-(fluoromethyl)-1-(2-methyl-3-(trifluoromethyl)benzyl)-6-morpholino-1H-benzo[d]imidazol-4-yl)boronic acid a) 4-bromo-2-(fluoromethyl)-6-nitro-1H-benzo[d]imidazole

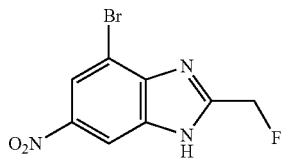 [SMILES: O=[N+]([O-])c1cc(Br)c2nc(CF)[nH]c2c1]

To a 250 mL round bottomed flask was added 3-bromo-5-nitrobenzene-1,2-diamine (6.75 g, 29.1 mmol) and 2-fluoroacetic acid (4.54 g, 58.2 mmol) in Toluene (100 mL). The solution was heated to reflux 48 h. The reaction was found to be incomplete so an additional equivalent of acid (2.25 g) was added and solution was heated 6 hours. The mixture was allowed to cool and was evaporated. The residue was dissolved in 20 ml of DCM and was filtered through a sintered glass funnel where a brown precipitate (5.5 g, 69%) was isolated to obtain 4-bromo-2-(fluoromethyl)-6-nitro-1H-benzo[d]imidazole (6.01 g, 21.93 mmol, 75% yield). $^1$H NMR (400 MHz, DMSO-d$_6$) δ ppm 5.69 (s, 1H) 5.81 (s, 1H) 8.33 (d, J=2.02 Hz, 1H) 8.49 (br. s., 1H); LC/MS: MS (ES$^+$) m/e 275 [M+H]$^+$.

b) 4-bromo-2-(fluoromethyl)-1-(2-methyl-3-(trifluoromethyl)benzyl)-6-nitro-1H-benzo[d]imidazole

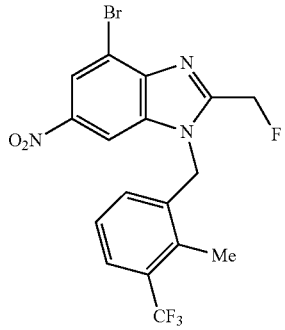

Into a 250 ml of round bottom flask with 4-bromo-2-(fluoromethyl)-6-nitro-1H-benzo[d]imidazole (3 g, 10.95 mmol) in N,N-Dimethylformamide (DMF) (50 mL) was added 1-(bromomethyl)-2-methyl-3-(trifluoromethyl)benzene (4.16 g, 16.42 mmol) and potassium carbonate (4.54 g, 32.8 mmol). The resulting reaction mixture was stirred 1 h at 80° C., cooled to room temperature and poured into water, extracted with ethyl acetate, washed with water, brine, dried (MgSO$_4$) and evaporated. The residue was purified on a silica gel cartridge and eluted with a gradient of 0% ethyl acetate/hexanes to 80% over 10 column volumes. The expected compound was collected and evaporated to yield 4-bromo-2-(fluoromethyl)-1-(2-methyl-3-(trifluoromethyl)benzyl)-6-nitro-1H-benzo[d]imidazole (3.05 g, 6.84 mmol, 62.4% yield) as a brown solid. $^1$H NMR (400 MHz, CHLOROFORM-d) δ ppm 2.56 (s, 3H) 5.54-5.78 (m, 4H) 6.51 (d, J=7.83 Hz, 1H) 7.18 (t, J=7.83 Hz, 1H) 7.64 (d, J=7.83 Hz, 1H) 8.13 (d, J=1.77 Hz, 1H) 8.44 (d, 1H); LC/MS: MS (ES$^+$) m/e 447 [M+H]$^+$.

c) 4-bromo-2-(fluoromethyl)-1-(2-methyl-3-(trifluoromethyl)benzyl)-1H-benzo[d]imidazol-6-amine

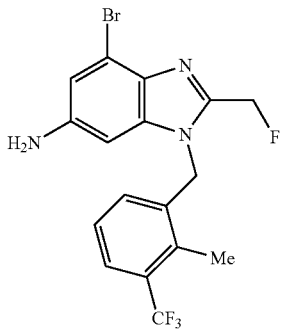 [SMILES: Cc1c(Cn2c(CF)nc3c(Br)cc([N+](=O)[O-])cc32)cccc1C(F)(F)F]

To a solution of 4-bromo-2-(fluoromethyl)-1-(2-methyl-3-(trifluoromethyl)benzyl)-6-nitro-1H-benzo[d]imidazole (3.05 g, 6.84 mmol) in Methanol (40 mL) in a 250 ml round bottomed flask was added Tin(II)chloride dihydrate (9.25 g, 41.0 mmol) and HCl (1.869 mL, 61.5 mmol). The reaction mixture was left to stir at 50° C. for 1 h; reaction mostly complete with a very small amt of starting material and a very small amt of des-fluoro product. The solvent was removed and diluted with water (100 mL) and this solution was decanted into a 250 mL Erlenmeyer flask. This solution was neutralized with 6N NaOH to pH 9—a white solid was observed. The brown residue in the rb flask was dissolved in 100 mL of EtOAc and washed with 1N NaOH, brine, dried and evaporated to yield a brown oil. The water layer was extracted with EtOAc to which yielded an additional oil. The oils were combined and purified by reversed phase HPLC; eluted with a gradient of acetonitrile (0.1% TFA) and water (0.1% TFA v/v) (25-70%) over 12 minutes. The fractions were collected and evaporated to yield the expected compound 4-bromo-2-(fluoromethyl)-1-(2-methyl-3-(trifluoromethyl)benzyl)-1H-benzo[d]imidazol-6-amine (2.3 g, 5.53 mmol, 81% yield). $^1$H NMR (400 MHz, CHLOROFORM-d) δ ppm 2.54 (s, 3H) 5.39 (s, 2H) 5.51 (s, 1H) 5.63 (s, 1H) 6.32 (d, J=2.02 Hz, 1H) 6.56 (d, J=7.83 Hz, 1H) 6.96 (d, J=2.02 Hz, 1H) 7.16 (t, J=7.83 Hz, 1H) 7.61 (d, J=7.83 Hz, 1H); LC/MS: MS (ES$^+$) m/e 417 [M+H]$^+$.

d) 4-(4-bromo-2-(fluoromethyl)-1-(2-methyl-3-(trifluoromethyl)benzyl)-1H-benzo[d]imidazol-6-yl)morpholine

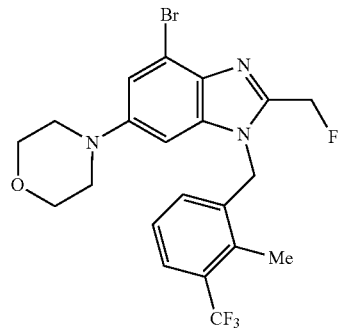 [SMILES: Cc1c(Cn2c(CF)nc3c(Br)cc(N4CCOCC4)cc32)cccc1C(F)(F)F]

Into a 100 ml round bottomed flask with 4-bromo-2-(fluoromethyl)-1-(2-methyl-3-(trifluoromethyl)benzyl)-1H-benzo[d]imidazol-6-amine (2.3 g, 5.53 mmol), tetrabutylammonium iodide (0.102 g, 0.276 mmol) was added 6N sodium hydroxide (13.82 ml, 83 mmol) and 1-bromo-2-(2-bromoethoxy)ethane (1.378 ml, 11.05 mmol). Reaction was heated to 110° C. for 2 h then cooled to room temperature and the mixture was extracted with EtOAc, washed with Brine and concentrated. The residue was purified on a silica gel cartridge and eluted with a gradient of 0% ethyl acetate/hexanes to 50% over 10 column volumes. The appropriate fractions were collected and evaporated to yield 4-(4-bromo-2-(fluoromethyl)-1-(2-methyl-3-(trifluoromethyl)benzyl)-1H-benzo[d]imidazol-6-yl)morpholine (911 mg, 1.873 mmol, 33.9% yield). $^1$H NMR (400 MHz, CHLOROFORM-d) δ ppm 2.51 (s, 3H) 3.04-3.11 (m, 4H) 3.77-3.85 (m, 4H) 5.40 (s, 2H) 5.42-5.60 (m, 2H) 6.45 (d, J=2.02 Hz, 1H) 6.53 (d, 1H) 7.12 (t, J=7.83 Hz, 1H) 7.21 (d, J=2.02 Hz, 1H) 7.56 (d, J=7.83 Hz, 1H); LC/MS: MS (ES$^+$) m/e 487 [M+H]$^+$.

e) (2-(fluoromethyl)-1-(2-methyl-3-(trifluoromethyl)benzyl)-6-morpholino-1H-benzo[d]imidazol-4-yl)boronic acid The titled compound was prepared from 4-(4-bromo-2-(fluoromethyl)-1-(2-methyl-3-(trifluoromethyl)benzyl)-1H-benzo[d]imidazol-6-yl)morpholine (400 mg, 0.823 mmol) using Method B to give the product (20 mg, 0.043 mmol, 5.23% yield), which was lyophilized to provide a white powder. $^1$H NMR (400 MHz, METHANOL-d$_4$) δ ppm 2.58 (s, 3H) 3.04-3.18 (m, 4H) 3.75-3.87 (m, 4H) 5.51-5.78 (m, 4H) 6.58 (d, 1H) 6.84 (br. s., 1H) 7.20 (t, J=7.83 Hz, 1H) 7.25-7.33 (m, 1H) 7.61 (d, J=7.83 Hz, 1H); LC/MS: MS (ES$^+$) m/e 452 [M+H]$^+$

Example 17

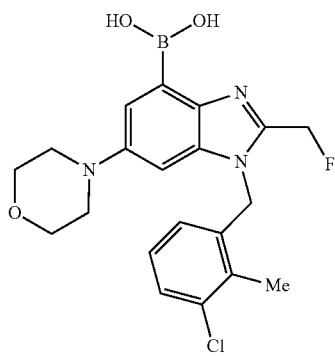 [SMILES: Cc1c(Cl)cccc1Cn1c(CF)nc2c(B(O)O)cc(N3CCOCC3)cc21]

Preparation of (1-(3-chloro-2-methylbenzyl)-2-(fluoromethyl)-6-morpholino-1H-benzo[d]imidazol-4-yl) boronic acid a) 4-bromo-1-(3-chloro-2-methylbenzyl)-2-(fluoromethyl)-6-nitro-1H-benzo[d]imidazole

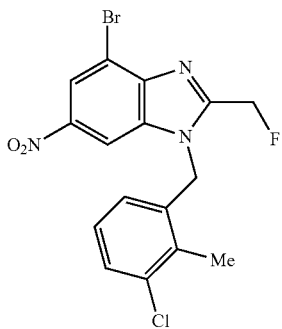 [SMILES: Cc1c(Cl)cccc1Cn1c(CF)nc2c(Br)cc([N+](=O)[O-])cc21]

Into a 250 ml flask with 4-bromo-2-(fluoromethyl)-6-nitro-1H-benzo[d]imidazole (3 g, 10.95 mmol) in N,N-Dimethylformamide (DMF) (100 mL) was added 1-(bromomethyl)-3-chloro-2-methylbenzene (3.60 g, 16.42 mmol) and potassium carbonate (4.54 g, 32.8 mmol). The resulting reaction mixture was stirred 1 h at 80° C., cooled to room temperature and poured into water, extracted with ethyl acetate, washed with water, brine, dried (MgSO$_4$) and evaporated. The residue was purified on a silica gel cartridge and eluted with a gradient of 0% ethyl acetate/hexanes to 80% over 10 column volumes. The expected compound was collected and evaporated to yield 4-bromo-1-(3-chloro-2-methylbenzyl)-2-(fluoromethyl)-6-nitro-1H-benzo[d]imidazole (1.23 g, 2.98 mmol, 27.2% yield) as a brown solid. $^1$H NMR (400 MHz, DMSO-d$_6$) δ ppm 2.48 (s, 3H) 5.71 (s, 1H) 5.83 (s, 1H) 5.85 (s, 2H) 6.10 (d, J=7.58 Hz, 1H) 7.05 (t, J=7.83 Hz, 1H) 7.38 (d, J=7.83 Hz, 1H) 8.39 (d, J=2.02 Hz, 1H) 8.67 (d, 1H); LC/MS: MS (ES$^+$) m/e 413 [M+H]$^+$.

b) 4-bromo-1-(3-chloro-2-methylbenzyl)-2-(fluoromethyl)-1H-benzo[d]imidazol-6-amine

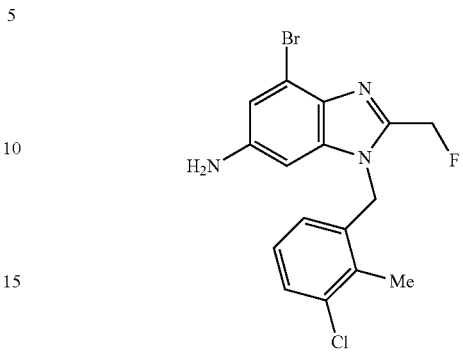

To a solution of 4-bromo-1-(3-chloro-2-methylbenzyl)-2-(fluoromethyl)-6-nitro-1H-benzo[d]imidazole (2.83 g, 6.86 mmol) in Methanol (40 mL) in a 250 ml round bottomed flask was added Tin(II)chloride dihydrate (9.29 g, 41.1 mmol) and HCl (1.875 mL, 61.7 mmol). The reaction mixture was left to stir at 50° for 3 h. The solvent was removed and diluted with water (100 mL) and this solution was decanted into a 250 mL Erlenmeyer flask. The brown residue remaining in the round bottomed flask was dissolved in 100 mL of EtOAc, washed with 1N NaOH, brine, dried and evaporated to yield a brown solid which was the expected compound 4-bromo-1-(3-chloro-2-methylbenzyl)-2-(fluoromethyl)-1H-benzo[d]imidazol-6-amine (2.49 g, 6.51 mmol, 95% yield). $^1$H NMR (400 MHz, CHLOROFORM-d) δ ppm 2.45-2.48 (m, 3H) 5.33 (s, 2H) 5.47 (s, 1H) 5.58-5.62 (m, 1H) 6.28-6.33 (m, 2H) 6.93 (d, J=1.77 Hz, 1H) 6.98 (s, 1H) 7.28 (s, 1H) 7.32 (d, 2H). LC/MS: MS (ES$^+$) m/e 383 [M+H]$^+$.

c) 4-(4-bromo-1-(3-chloro-2-methylbenzyl)-2-(fluoromethyl)-1H-benzo[d]imidazol-6-yl)morpholine

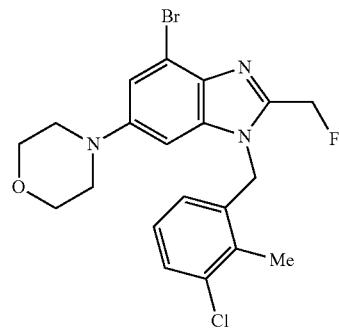 [SMILES: Cc1c(Cl)cccc1Cn1c(CF)nc2c(Br)cc(N3CCOCC3)cc21]

Into a 100 ml round bottomed flask with 4-bromo-1-(3-chloro-2-methylbenzyl)-2-(fluoromethyl)-1H-benzo[d]imidazol-6-amine (2.49 g, 6.51 mmol), tetrabutylammonium iodide (0.120 g, 0.325 mmol) was added 6N sodium hydroxide (16.27 ml, 98 mmol) and 1-bromo-2-(2-bromoethoxy) ethane (1.623 ml, 13.01 mmol), Reaction was heated to 110° C. for 2 h then cooled to room temperature and the mixture was extracted with EtOAc, washed with Brine and concentrated. The residue was purified by reversed phase eluted with a gradient of acetonitrile (0.1% TFA) and water (0.1% TFA v/v) (35-65%) over 12 minutes. The expected compound was collected and evaporated to yield a colorless oil 4-(4-bromo-1-(3-chloro-2-methylbenzyl)-2-(fluoromethyl)-1H-benzo[d]imidazol-6-yl)morpholine (777 mg, 1.716 mmol, 26.4% yield). $^1$H NMR (400 MHz, METHANOL-$d_4$) δ ppm 2.50 (s, 3H) 3.12-3.18 (m, 4H) 3.78-3.86 (m, 4H) 5.55-5.71 (m, 4H) 6.37 (d, J=8.08 Hz, 1H) 6.84 (d, J=2.02 Hz, 1H) 7.06 (t, J=8.08 Hz, 1H) 7.36 (d, J=8.08 Hz, 1H) 7.39 (d, 1H); LC/MS: MS (ES$^+$) m/e 453 [M+H]$^+$.

d) (1-(3-chloro-2-methylbenzyl)-2-(fluoromethyl)-6-morpholino-1H-benzo[d]imidazol-4-yl)boronic acid The titled compound was prepared from 4-(4-bromo-1-(3-chloro-2-methylbenzyl)-2-(fluoromethyl)-1H-benzo[d]imidazol-6-yl)morpholine (300 mg, 0.663 mmol) using Method A with trimethylborate to give the product (9.1 mg, 0.020 mmol, 3.09% yield) after lyophilization from water. $^1$H NMR (400 MHz, METHANOL-$d_4$) δ ppm 2.53 (s, 3H) 3.20 (d, J=4.80 Hz, 4H) 3.81-3.86 (m, 4H) 5.75 (s, 1H) 5.83 (s, 2H) 5.86-5.90 (m, 1H) 6.44-6.49 (m, 1H) 6.99-7.03 (m, 1H) 7.09 (s, 1H) 7.39 (s, 1H) 7.58 (s, 1H); LC/MS: MS (ES$^+$) m/e 418 [M+H]$^+$.

Example 18

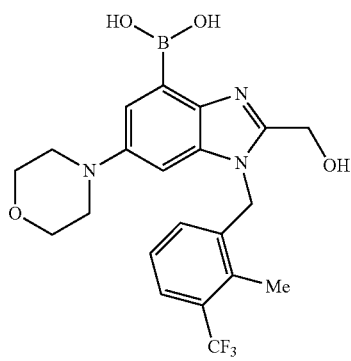 [SMILES: Cc1c(Cn2c(CO)nc3c(B(O)O)cc(N4CCOCC4)cc32)cccc1C(F)(F)F]

Preparation of (2-(hydroxymethyl)-1-(2-methyl-3-(trifluoromethyl)benzyl)-6-morpholino-1H-benzo[d]imidazol-4-yl)boronic acid (2-(fluoromethyl)-1-(2-methyl-3-(trifluoromethyl)benzyl)-6-morpholino-1H-benzo[d]imidazol-4-yl)boronic acid (40 mg, 0.089 mmol) was dissolved in Water+0.1% TFA (2.5 mL) and Acetonitrile+0.1% TFA (2.5 mL) in a 20 mL scintillation vial. The mixture was stirred at 70° C. for 2 days, solution was evaporated and taken up in 50% water/acetonitrile and was purified by reversed phase HPLC eluted with a gradient of acetonitrile (0.1% TFA) and water (0.1% TFA v/v) (20-55%) over 12 minutes. The appropriate fractions were collected and evaporated to yield (2-(hydroxymethyl)-1-(2-methyl-3-(trifluoromethyl)benzyl)-6-morpholino-1H-benzo[d]imidazol-4-yl)boronic acid (18.5 mg, 0.041 mmol, 46.0% yield). $^1$H NMR (400 MHz, METHANOL-$d_4$) δ ppm 2.59 (s, 3H) 3.11-3.21 (m, 4H) 3.75-3.86 (m, 4H) 5.04 (s, 2H) 5.88 (s, 2H) 6.75 (d, 1H) 7.03 (d, J=2.27 Hz, 1H) 7.25 (t, J=7.83 Hz, 1H) 7.65 (d, J=7.83 Hz, 1H) 7.72 (br. s., 1H); LC/MS: MS (ES$^+$) m/e 450 [M+H]$^+$.

Example 19

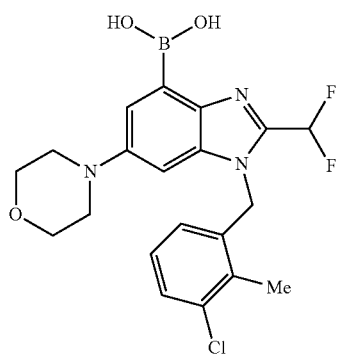 [SMILES: Cc1c(Cl)cccc1Cn1c(C(F)F)nc2c(B(O)O)cc(N3CCOCC3)cc21]

Preparation of (1-(3-chloro-2-methylbenzyl)-2-(difluoromethyl)-6-morpholino-1H-benzo[d]imidazol-4-yl)boronic acid a) 4-bromo-2-(difluoromethyl)-6-nitro-1H-benzo[d]imidazole

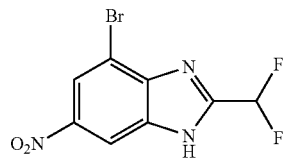 [SMILES: O=[N+]([O-])c1cc(Br)c2nc(C(F)F)[nH]c2c1]

To a 100 mL round bottomed flask was added 3-bromo-5-nitrobenzene-1,2-diamine (5.5 g, 23.70 mmol) and 2,2-difluoroacetic acid (4.46 mL, 71.1 mmol) in Toluene (55 mL). The stirred solution was heated to 105° C. and monitored by LC/MS. After stirring at 105° C. for 2 hr the reaction was allowed to cool to rt, was diluted with EtOAc (20 mL) and filtered through celite. The filtrate was concentrated in-vacuo then taken up in EtOAc, washed several times with sat'd NaHCO$_3$ soln, brine and then dried over Na$_2$SO$_4$ and concentrated to provide crude 4-bromo-2-(difluoromethyl)-6-nitro-1H-benzo[d]imidazole (6.7 g, 22.94 mmol, 97% yield) as a brown solid. LC/MS: MS (ES$^+$) m/e 293.7 [M+H]$^+$.

b) 4-bromo-1-(3-chloro-2-methylbenzyl)-2-(difluoromethyl)-6-nitro-1H-benzo[d]imidazole

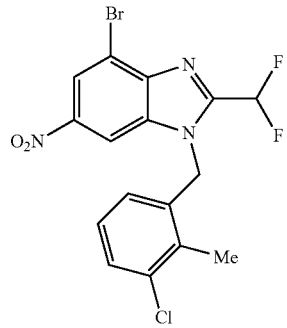

To a 100 mL round bottomed flask containing DMF (17 mL) was added 4-bromo-2-(difluoromethyl)-6-nitro-1H-benzo[d]imidazole (2.3 g, 7.88 mmol), 1-(bromomethyl)-3-chloro-2-methylbenzene (2.4 g, 10.93 mmol) and potassium carbonate (2.3 g, 16.64 mmol). The resultant suspension was heated to 70° C. and after stirring for 20 minutes LC/MS indicated that almost all starting material had been consumed so the heat was turned off and the reaction was allowed to stir overnight at rt. The next day the mixture was diluted with 75 mL H$_2$O and stirred for 10 minutes resulting in the precipitation of a light brown solid. The solid was isolated by filtration and was washed 3× with H$_2$O and 3× with hexanes to provide 4-bromo-1-(3-chloro-2-methylbenzyl)-2-(difluoromethyl)-6-nitro-1H-benzo[d]imidazole (4.2 g, 8.39 mmol, 107% yield) as light brown solid. The NMR and LC/MS were consistent with desired product and the crude product will be used in subsequent reactions without further purification. LC/MS: MS (ES$^+$) m/e 431.9 [M+H]$^+$; $^1$H NMR (400 MHz, DMSO-d$_6$) δ ppm 8.76 (d, J=2.02 Hz, 1H), 8.45 (d, J=2.02 Hz, 1H), 7.32-7.68 (m, 2H), 6.99-7.12 (m, 1H), 6.06 (d, J=7.58 Hz, 1H), 5.90 (s, 2H), 2.47 (s, 3H)

c) 4-bromo-1-(3-chloro-2-methylbenzyl)-2-(difluoromethyl)-1H-benzo[d]imidazol-6-amine

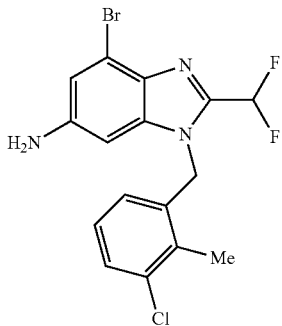 [SMILES: Cc1c(Cl)cccc1Cn1c(C(F)F)nc2c(Br)cc([N+](=O)[O-])cc21]

To a 250 mL rb flask containing MeOH (50 mL) was added 4-bromo-1-(3-chloro-2-methylbenzyl)-2-(difluoromethyl)-6-nitro-1H-benzo[d]imidazole (4.0 g, 9.29 mmol), tin(II) chloride dihydrate (12.58 g, 55.7 mmol) and concentrated hydrochloric acid (6.97 ml, 84 mmol). The resultant suspension was heated to 50° C. and monitored by LC/MS. By LC/MS the reaction was complete in 45 minutes. After the reaction had cooled to room temperature and was filtered to remove insoluble tin salts, 6N NaOH (0.8 ml, 4.00 mmol) was added to adjust the pH to about 11 and the mixture was concentrated to remove any MeOH. The sticky mixture was extracted with EtOAC; however, because it was difficult to extract from the tin-salt containing aqueous the entire mixture of two phases was filtered then the layers were separated. The organic was dried over MgSO$_4$ and concentrated in vacuo to provide and the organic was washed with H$_2$O and brine and dried over MgSO$_4$ and filtered. The solvent was removed in-vacuo leaving light brown solid 4-bromo-1-(3-chloro-2-methylbenzyl)-2-(difluoromethyl)-1H-benzo[d]imidazol-6-amine (2.25 g, 5.62 mmol, 60.5% yield) as crude material. LC/MS: MS (ES$^+$) m/e 402.4 [M+H]$^+$; $^1$H NMR (400 MHz, CHLOROFORM-d) δ ppm 7.33 (d, J=7.83 Hz, 1H), 6.80-7.13 (m, 3H), 6.33 (d, J=7.83 Hz, 1H), 6.25 (d, J=2.02 Hz, 1H), 5.46 (s, 2H), 3.81 (s, 2H), 2.49 (s, 3H)

d) 4-(4-bromo-1-(3-chloro-2-methylbenzyl)-2-(difluoromethyl)-1H-benzo[d]imidazol-6-yl)morpholine

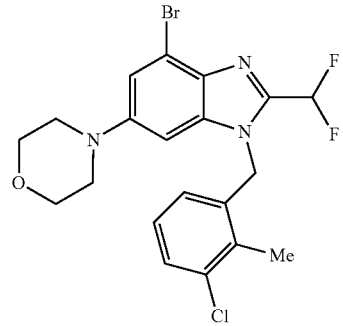 [SMILES: Cc1c(Cl)cccc1Cn1c(C(F)F)nc2c(Br)cc(N3CCOCC3)cc21]

The crude product from the previous reaction 4-bromo-1-(3-chloro-2-methylbenzyl)-2-(difluoromethyl)-1H-benzo[d]imidazol-6-amine (2.25 g, 5.62 mmol) was stirred in 6M sodium hydroxide (30 mL, 180 mmol) solution with 1-bromo-2-(2-bromoethoxy)ethane (1.5 mL, 12.03 mmol) and tetrabutylammonium iodide (0.207 g, 0.562 mmol) at 110° C. After stirring for 2.5 hr the mixture was cooled and the aqueous was decanted and the remaining sticky solid was dissolved in EtOAc. The organic was washed with H$_2$O and brine, and dried over MgSO$_4$ and concentrated to leave a residue that was purified by column chromatography. The residue was loaded onto a 25 g Silica column and eluted with EtOAc/Hex 10% to 40% over 15 minutes. The cleanest fractions containing desired product were combined and concentrated in-vacuo to afford 892 mg (34% yield) of the titled compound. LC/MS: MS (ES$^+$) m/e 471.8 [M+H]$^+$; $^1$H NMR (400 MHz, CHLOROFORM-d) δ ppm 7.22-7.37 (m, 3H), 6.81-7.14 (m, 2H), 6.31-6.42 (m, 2H), 5.51 (s, 2H), 3.76-3.89 (m, 4H), 3.03-3.20 (m, 4H), 2.48 (s, 3H)

e) (1-(3-chloro-2-methylbenzyl)-2-(difluoromethyl)-6-morpholino-1H-benzo[d]imidazol-4-yl)boronic acid The titled compound was prepared from 4-(4-bromo-1-(3-chloro-2-methylbenzyl)-2-(difluoromethyl)-1H-benzo[d]imidazol-6-yl)morpholine (430 mg, 0.913 mmol) using Method A with trimethylborate to give the product (55 mg, 0.126 mmol, 13.82% yield) as a light brown solid. LC/MS: MS (ES$^+$) m/e 436.2 [M+H]$^+$; $^1$H NMR (400 MHz, METHANOL-d$_4$) δ ppm 7.44-7.58 (m, 1H), 7.27-7.38 (m, 1H), 7.15 (d, J=2.27 Hz, 1H), 7.00 (t, J=7.96 Hz, 1H), 6.26 (d, J=7.58 Hz, 1H), 5.75 (s, 2H), 3.81-3.94 (m, 4H), 2.50 (s, 3H)

Example 20

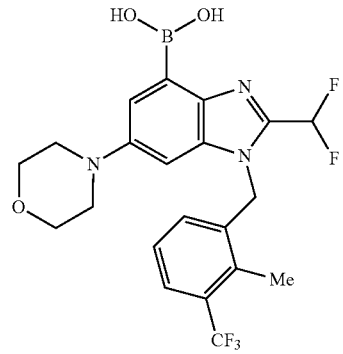 [SMILES: Cc1c(Cn2c(C(F)F)nc3c(B(O)O)cc(N4CCOCC4)cc32)cccc1C(F)(F)F]

Preparation of (2-(difluoromethyl)-1-(2-methyl-3-(trifluoromethyl)benzyl)-6-morpholino-1H-benzo[d]imidazol-4-yl)boronic acid a) 4-bromo-2-(difluoromethyl)-1-(2-methyl-3-(trifluoromethyl)benzyl)-6-nitro-1H-benzo[d]imidazole

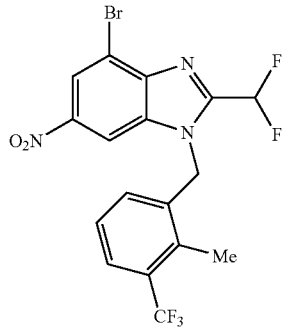 [SMILES: Cc1c(Cn2c(C(F)F)nc3c(Br)cc([N+](=O)[O-])cc32)cccc1C(F)(F)F]

To a 100 mL round bottomed flask containing DMF (30 mL) was added 4-bromo-2-(difluoromethyl)-6-nitro-1H-benzo[d]imidazole (3.2 g, 10.96 mmol), 1-(bromomethyl)-2-methyl-3-(trifluoromethyl)benzene (1.60 mL, 9.48 mmol) and potassium carbonate (2.3 g, 16.64 mmol). The resultant suspension was heated to 65° C. and after stirring for 2 hrs the mixture was allowed to cool to rt and diluted with 35 mL H$_2$O. The resulting slurry was extracted several times with EtOAc, the organic dried over Na$_2$SO$_4$ and concentrated to give a thick oil which was adsorbed onto a silical gel column and was eluted with EtOAc/Hex 10% to 20% gradient over 15 column volumes on a 25 g silica column. The fractions containing desired product were combined and concentrated desired product (1.54 g, 3.32 mmol, 30.3% yield) as a light orange powder. LC/MS: MS (ES$^+$) m/e 464.2 [M+H]$^+$; $^1$H NMR (400 MHz, CHLOROFORM-d) δ ppm 8.52 (d, J=1.77 Hz, 1H), 8.07 (d, J=2.02 Hz, 1H), 7.66 (d, J=7.83 Hz, 1H), 7.20 (d, J=3.79 Hz, 1H), 7.07 (s, 1H), 6.94 (s, 1H), 6.52 (d, J=8.08 Hz, 1H), 5.73 (s, 2H), 2.58 (s, 3H).

b) 4-bromo-2-(difluoromethyl)-1-(2-methyl-3-(trifluoromethyl)benzyl)-1H-benzo[d]imidazol-6-amine

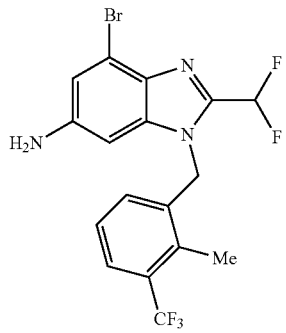

A mixture of 4-bromo-2-(difluoromethyl)-1-(2-methyl-3-(trifluoromethyl)benzyl)-6-nitro-1H-benzo[d]imidazole (830 mg, 1.788 mmol) and zinc (701 mg, 10.73 mmol) in Acetic Acid (15 mL) was stirred and heated to 60° C. The reaction was monitored by LC/MS. After 90 minutes, a substantial amount of desired product was detected by LC/MS. The reaction was allowed to sit overnight and the next day the mixture was filtered through celite washing with HOAc. The filtrate was concentrated in-vacuo and the resulting residue, while appearing relatively clean and homogeneous by LC/MS, was a mixture of 2 compounds as indicated by TLC. The residue was loaded on a 10 g silica column and eluted with 12% EtOAc/hex for 6 column volumes then a gradient was run from 12% to 35% EtOAc/hex over 15 column volumes successfully separating the two closely eluting compounds. The early eluting compound was the desired product and the fractions were combined and concentrated to give 4-bromo-2-(difluoromethyl)-1-(2-methyl-3-(trifluoromethyl)benzyl)-1H-benzo[d]imidazol-6-amine (310 mg, 0.714 mmol, 39.9% yield) as a light yellow solid. LC/MS: MS (ES$^+$) m/e 434.3 [M+H]$^+$; $^1$H NMR (400 MHz, CHLOROFORM-d) δ ppm 7.56 (d, J=7.83 Hz, 1H), 7.12 (t, J=7.83 Hz, 1H), 7.06 (s, 1H), 6.86-7.01 (m, 2H), 6.80 (s, 1H), 6.52 (d, J=7.83 Hz, 1H), 6.23 (d, J=2.02 Hz, 1H), 5.46 (s, 2H), 2.52 (s, 3H)

c) 4-(4-bromo-2-(difluoromethyl)-1-(2-methyl-3-(trifluoromethyl)benzyl)-1H-benzo[d]imidazol-6-yl)morpholine

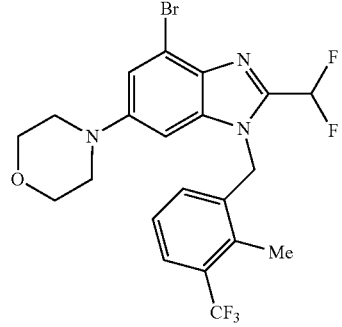 [SMILES: Cc1c(Cn2c(C(F)F)nc3c(Br)cc(N4CCOCC4)cc32)cccc1C(F)(F)F]

Two combined batches of 4-bromo-2-(difluoromethyl)-1-(2-methyl-3-(trifluoromethyl)benzyl)-1H-benzo[d]imidazol-6-amine (1.087 g, 2.503 mmol) was stirred in 6M sodium hydroxide (30 mL, 180 mmol) solution with 1-bromo-2-(2-bromoethoxy)ethane (1.5 mL, 12.03 mmol) and tetrabutylammonium iodide (0.092 g, 0.250 mmol) at 110° C. After stirring for 2.5 hr the mixture was cooled and the aqueous was decanted and the remaining sticky solid was dissolved in EtOAc. The organic was washed with H$_2$O and brine and dried over MgSO$_4$ and concentrated to leave a residue. The residue was loaded onto a 25 g Silica column and eluted with a EtOAc/Hex 15% to 40% over 15 column volumes. While loading onto the column, a significant amount of solid crystallized on the silica wafer. This material was scraped off and dried in-vacuo to provide 4-(4-bromo-2-(difluoromethyl)-1-(2-methyl-3-(trifluoromethyl)benzyl)-1H-benzo[d]imidazol-6-yl)morpholine (458 mg, 0.908 mmol, 36.3% yield) as a light orange solid. The material that was absorbed on the silica wafer was purified to provide additional material 4-(4-bromo-2-(difluoromethyl)-1-(2-methyl-3-(trifluoromethyl)benzyl)-1H-benzo[d]imidazol-6-yl)morpholine (300 mg, 0.595 mmol, 23.76% yield). The total yield desired product was 758 mg (60%). LC/MS: MS (ES$^+$) m/e 503.9 [M+H]$^+$; $^1$H NMR (400 MHz, CHLOROFORM-d) δ ppm 7.61 (d, J=7.83 Hz, 1H), 7.25-7.32 (d, J=1.77 Hz, 1H), 7.16 (t, J=7.83 Hz, 1H), 6.83-7.13 (m, 1H), 6.59 (d, J=7.58 Hz, 1H), 6.38 (d, J=1.77 Hz, 1H), 5.55 (s, 2H), 3.77-3.92 (m, 4H), 3.05-3.16 (m, 4H), 2.56 (s, 3H)

d) (2-(difluoromethyl)-1-(2-methyl-3-(trifluoromethyl)benzyl)-6-morpholino-1H-benzo[d]imidazol-4-yl)boronic acid The titled compound was prepared from 4-(4-bromo-2-(difluoromethyl)-1-(2-methyl-3-(trifluoromethyl)benzyl)-1H-benzo[d]imidazol-6-yl)morpholine (620 mg, 1.29 mmol) using Method B to give the desired product (153 mg, 0.310 mmol, 25.2% yield). The NMR and LC/MS were consistent with structure and indicated that there was a minor amount (~5%) of des-boronylated product in the sample. LC/MS: MS (ES+) m/e 470.3 [M+H]+; 1H NMR (400 MHz, METHANOL-d4) δ ppm 7.58 (d, J=7.58 Hz, 1H), 7.17 (t, J=7.71 Hz, 2H), 7.04 (s, 1H), 6.81 (s, 1H), 6.49 (d, J=7.83 Hz, 1H), 5.72 (s, 2H), 3.70-3.90 (m, 4H), 3.01-3.16 (m, 4H), 2.56 (s, 3H).

Example 21

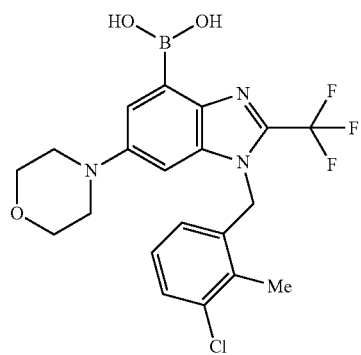 [SMILES: Cc1c(Cl)cccc1Cn1c(C(F)(F)F)nc2c(B(O)O)cc(N3CCOCC3)cc21]

Preparation of (1-(3-chloro-2-methylbenzyl)-6-morpholino-2-(trifluoromethyl)-1H-benzo[d]imidazol-4-yl)boronic acid a) 4-bromo-6-nitro-2-(trifluoromethyl)-1H-benzo[d]imidazole

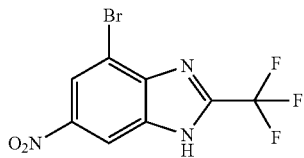 [SMILES: O=[N+]([O-])c1cc(Br)c2nc(C(F)(F)F)[nH]c2c1]

In a 250 mL round-bottom flask a mixture of 3-bromo-5-nitrobenzene-1,2-diamine (10 g, 43.1 mmol) and TFA (23.24 mL, 302 mmol) was heated to 85° C. for 17 hours. The mixture was allowed to cool to RT, and then was concentrated in vacuo to remove the excess TFA. The residue was partitioned between water (100 mL) and ether (100 mL; not soluble in dichloromethane). The phases were separated, and the organic layer was dried over Na2SO4, then filtered and concentrated in vacuo to provide 4-bromo-6-nitro-2-(trifluoromethyl)-1H-benzo[d]imidazole (7.1 g, 22.90 mmol, 53.1% yield) as a brown solid. LCMS and NMR are consistent with structure (NMR contains a trace of ether). MS (ES+) m/e: 308.9, 310.1 [M+H]+; 1H NMR (400 MHz, DMSO-d6) δ ppm 15.09 (br. s., 1H) 8.49-8.66 (m, 1H) 8.36-8.48 (m, 1H)

b) 4-bromo-1-(3-chloro-2-methylbenzyl)-6-nitro-2-(trifluoromethyl)-1H-benzo[d]imidazole

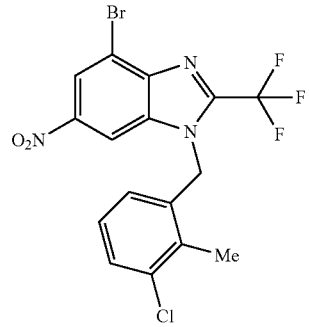 [SMILES: Cc1c(Cl)cccc1Cn1c(C(F)(F)F)nc2c(Br)cc([N+](=O)[O-])cc21]

Charged a 100 mL round bottom flask containing 4-bromo-6-nitro-2-(trifluoromethyl)-1H-benzo[d]imidazole (4.3 g, 13.87 mmol) dissolved in N,N-Dimethylformamide (DMF) (30 mL) with 1-(bromomethyl)-3-chloro-2-methylbenzene (3.81 g, 17.34 mmol) then added potassium carbonate (4.79 g, 34.7 mmol). The resulting reaction suspension was stirred for 6 h at 90° C., then cooled to RT, and filtered to remove potassium carbonate. The resulting filtrate was concentrated to a small volume (~10 mL), and diluted with water. The aqueous suspension was extracted with chloroform (3×), the organic extracts were combined, washed with brine, dried over Na2SO4, filtered, and finally concentrated in vacuo. The crude solid was slurried in hexane to provide 4-bromo-1-(3-chloro-2-methylbenzyl)-6-nitro-2-(trifluoromethyl)-1H-benzo[d]imidazole (3.5 g, 7.80 mmol, 56.2% yield). The material was carried onto the nitro reduction without further purification. MS (ES+) m/e: 449.0, 450.8 [M+H]+(bromine pattern). 1H NMR (400 MHz, CHLOROFORM-d) δ ppm 8.55 (d, J=2.02 Hz, 1H) 8.08 (d, J=1.77 Hz, 1H) 7.40 (d, J=8.08 Hz, 1H) 7.04 (t, J=7.96 Hz, 1H) 6.23 (d, J=7.83 Hz, 1H) 5.63 (s, 2H) 2.52 (s, 3H)

c) 4-bromo-1-(3-chloro-2-methylbenzyl)-2-(trifluoromethyl)-1H-benzo[d]imidazol-6-amine

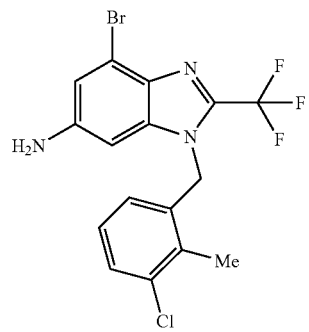

To a 100 mL round-bottom flask containing MeOH (25 mL) was added 4-bromo-1-(3-chloro-2-methylbenzyl)-6-nitro-2-(trifluoromethyl)-1H-benzo[d]imidazole (5.3 g, 11.81 mmol), tin(II) chloride dihydrate (8.00 g, 35.4 mmol) and hydrochloric acid (4.92 mL, 59.1 mmol). The resultant suspension was heated to 50° C. and monitored by LC/MS. By LC/MS the reaction was complete in 30 minutes. After the reaction had cooled to room temperature, the majority of the MeOH was removed in-vacuo and 6N aqueous sodium hydroxide solution was added to adjust the pH to pH>10 and the mixture was extracted with ethyl acetate (50 mL). The organic layer was washed with $H_2O$ and brine then dried over $MgSO_4$ and filtered. The solvent was removed in vacuo and the crude solid was purified by chromatography on silica gel eluted with chloroform/(solution of 2N ammonia in methanol) [95:5]. The fractions corresponding to product were combined, then concentrated in vacuo to provide 4-bromo-1-(3-chloro-2-methylbenzyl)-2-(trifluoromethyl)-1H-benzo[d]imidazol-6-amine (3.78 g, 9.03 mmol, 76% yield) as a light yellow solid. MS (ES+) m/e: 419.0, 420.0 $[M+H]^+$; $^1H$ NMR (400 MHz, CHLOROFORM-d) δ ppm 7.34 (d, J=8.08 Hz, 1H) 6.95-7.05 (m, 2H) 6.21-6.32 (m, 2H) 5.39 (s, 2H) 3.84 (s, 2H) 2.49 (s, 3H)

d) 4-(4-bromo-1-(3-chloro-2-methylbenzyl)-2-(trifluoromethyl)-1H-benzo[d]imidazol-6-yl)morpholine

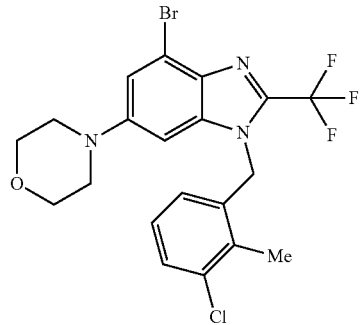 [SMILES: Cc1c(Cl)cccc1Cn1c(C(F)(F)F)nc2c(Br)cc(N3CCOCC3)cc21]

Into a 100 ml round bottomed flask charged with 4-bromo-1-(3-chloro-2-methylbenzyl)-2-(trifluoromethyl)-1H-benzo[d]imidazol-6-amine (3.1 g, 7.40 mmol) and tetrabutylammonium iodide (0.137 g, 0.370 mmol) was added 6N sodium hydroxide (18.51 ml, 111 mmol) and 1-bromo-2-(2-bromoethoxy)ethane (1.87 ml, 14.81 mmol). The reaction was heated to 110° C. and was monitored by LCMS. The reaction was complete after 2 h. The reaction was cooled to RT and the mixture was extracted with ethyl acetate (3×25 mL). The combined organic phase was washed with brine (30 mL), the organic extracts were combined, concentrated in vacuo, and the residue was purified by flash chromatography on silica gel eluted with a solution of (2N ammonia in methanol)/chloroform (0% to 10%). The fractions containing product were combined, then concentrated in vacuo to provide the desired product (1.62 g, 3.31 mmol, 44.8% yield) as a brown solid. NMR & LCMS were consistent with the structure. MS (ES+) m/e: 487.1, 488.1 $[M+H]^+$; $^1H$ NMR (400 MHz, CHLOROFORM-d) δ ppm 2.42 (s, 3H) 3.03-3.21 (m, 4H) 3.78-3.89 (m, 4H) 5.43 (s, 2H) 6.28 (d, J=7.58 Hz, 1H) 6.38 (d, J=2.02 Hz, 1H) 6.99 (t, J=7.96 Hz, 1H) 7.29 (d, J=2.27 Hz, 1H) 7.34 (d, J=7.83 Hz, 1H)

e) (1-(3-chloro-2-methylbenzyl)-6-morpholino-2-(trifluoromethyl)-1H-benzo[d]imidazol-4-yl)boronic acid To a solution of 4-(4-bromo-1-(3-chloro-2-methylbenzyl)-2-(trifluoromethyl)-1H-benzo[d]imidazol-6-yl)morpholine (1.38 g, 2.82 mmol) in THF (55 mL) stirring at −78° C. under nitrogen was slowly added 2.5M BuLi (2.259 mL, 5.65 mmol) via syringe. Immediately after the addition of n-BuLi, trimethyl borate (1.262 mL, 11.29 mmol) was added via syringe and then the dry ice bath was removed and the reaction was allowed to warm to room temperature. After stirring at RT for 60 minutes the mixture was quenched with MeOH and the entire reaction mixture was concentrated in vacuo to leave 2.1 g of crude reaction products—containing both the desired boronic acid and the des-bromo analog by LCMS with the desired boronic acid as the major product. The crude material was combined with crude material from a second reaction. The entire mixture was purified on silica gel that had been pre-treated with 3 column volumes of 0.5M ammonium acetate in methanol prior to being washed and equilibrated with chloroform. The column was eluted sequentially with chloroform/hexane (1:1, 300 mL) followed by chloroform (500 mL), then (a 2N solution of ammonia in methanol)/chloroform (5:95, 2 L). The fractions corresponding to product were combined and concentrated in vacuo to provide partially purified desired product that was free of the des-bromo analog by HPLC. The material was subsequently purified by preparative chiral phase HPLC. The product fractions were concentrated to provide an oil. Next added 200 ml $CHCl_3$ and 200 ml of aqueous 0.5 M $K_2HPO_4$ (pH 3.4) and mixed. Separated the two phases, and re-extracted the aqueous phase with 2×100 ml $CHCl_3$. Washed $CHCl_3$ layer with $H_2O$, then dried the $CHCl_3$ layer over $Na_2SO_4$, filtered and concentrated to leave a beige glassy solid. The solid was chased with ethyl acetate (2×50 ml), and then dried @ 50° C. under high vacuum (4.5 hr.) to give desired product (250 mg). MS (ES+) m/e: 453.1, 454.1 $[M+H]^+$; C18 HPLC 99.5%; $^1H$ NMR (400 MHz, METHANOL-$d_4$) δ ppm 2.51 (s, 3H) 3.05-3.22 (m, 4H) 3.70-3.93 (m, 4H) 5.67 (s, 2H) 6.19 (d, J=8.08 Hz, 1H) 6.84 (br. s., 1H) 7.02 (t, J=8.08 Hz, 1H) 7.19-7.30 (m, 1H) 7.34 (d, J=8.34 Hz, 1H).

Example 22

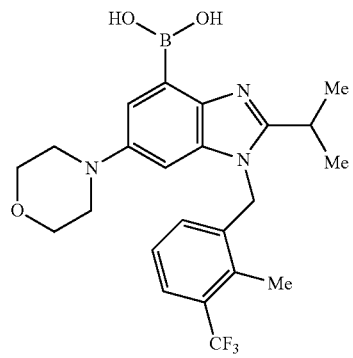 [SMILES: Cc1c(Cn2c(C(C)C)nc3c(B(O)O)cc(N4CCOCC4)cc32)cccc1C(F)(F)F]

Preparation of (2-isopropyl-1-(2-methyl-3-(trifluoromethyl)benzyl)-6-morpholino-1H-benzo[d]imidazol-4-yl)boronic acid a) 4-bromo-2-isopropyl-6-nitro-1H-benzo[d]imidazole

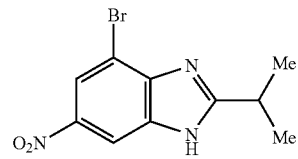 [SMILES: CC(C)c1nc2c(Br)cc([N+](=O)[O-])cc2[nH]1]

A mixture of 3-bromo-5-nitrobenzene-1,2-diamine (4 g, 17.24 mmol) and isobutyric acid (7.99 ml, 86 mmol) in 3M HCl (100 ml, 300 mmol) was heated to 105° C. for 5 days. The mixture was allowed to cool to room temperature and was poured into chilled 5M Sodium Hydroxide (60.0 ml, 300 mmol) solution. The resulting mixture was allowed to stand in an ice bath and the brown solid that precipitated was collected by filtration. The solid was washed several times with H$_2$O and then dried in a vacuum oven at 50° C. leaving desired product as a dark solid (4.2 g, 71% yield). MS (ES+) m/e: 283.0, 284.0 [M+H]+ b) 4-bromo-2-isopropyl-1-(2-methyl-3-(trifluoromethyl)benzyl)-6-nitro-1H-benzo[d]imidazole

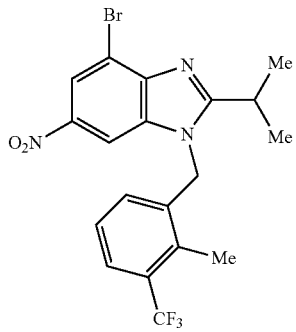

To a 100 mL round bottomed flask containing DMF (50 mL) was added 4-bromo-2-isopropyl-6-nitro-1H-benzo[d]imidazole (4.1 g, 14.43 mmol), 1-(bromomethyl)-2-methyl-3-(trifluoromethyl)benzene (3.6 mL, 21.34 mmol) and potassium carbonate (5.98 g, 43.3 mmol). The resultant suspension was heated to 50° C. and after stirring for 30 minutes the mixture was allowed to cool to rt and diluted with 100 mL H$_2$O. The mixture was stirred overnight and the next day a black filterable solid was isolated by filtration providing crude 4-bromo-2-isopropyl-1-(2-methyl-3-(trifluoromethyl)benzyl)-6-nitro-1H-benzo[d]imidazole (7.1 g, 15.56 mmol, 108% yield). MS (ES+) m/e: 455.1, 455.9 [M+H]+ c) 4-bromo-2-isopropyl-1-(2-methyl-3-(trifluoromethyl)benzyl)-1H-benzo[d]imidazol-6-amine

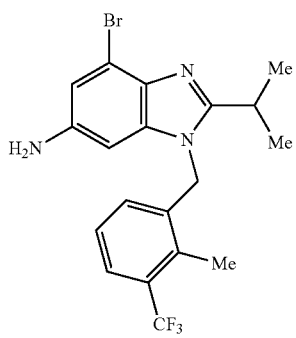 [SMILES: Cc1c(Cn2c(C(C)C)nc3c(Br)cc([N+](=O)[O-])cc32)cccc1C(F)(F)F]

To a 250 mL round-bottom flask containing MeOH (100 mL) was added crude 4-bromo-2-isopropyl-1-(2-methyl-3-(trifluoromethyl)benzyl)-6-nitro-1H-benzo[d]imidazole (7.1 g, 15.56 mmol), tin(II) chloride dihydrate (10.53 g, 46.7 mmol) and hydrochloric acid (6.48 mL, 78 mmol). The resultant suspension was heated to 60° C. and monitored by LC/MS. By LC/MS the reaction was complete in 30 minutes. After the reaction had cooled to rt, the majority of the MeOH was removed in-vacuo and sodium carbonate (150 mL, 150 mmol) was added slowly to adjust the pH to about 10 and the mixture was extracted with Et$_2$O (150 mL) and the organic was washed with H$_2$O and brine and dried over MgSO$_4$ and filtered. The solvent was removed in-vacuo leaving the desired product (4.7 g, 11.03 mmol, 70.9% yield) as crude brown solid that by LC/MS was sufficiently pure to use in the next step. MS (ES+) m/e: 425.1, 426.0 [M+H]+ d) 4-(4-bromo-2-isopropyl-1-(2-methyl-3-(trifluoromethyl)benzyl)-1H-benzo[d]imidazol-6-yl)morpholine

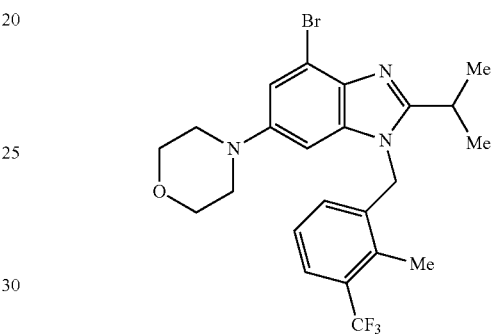

The product from previous reaction 4-bromo-2-isopropyl-1-(2-methyl-3-(trifluoromethyl)benzyl)-1H-benzo[d]imidazol-6-amine (4.7 g, 11.03 mmol) was stirred in 6M sodium hydroxide (100 mL, 600 mmol) solution with 1-bromo-2-(2-bromoethoxy)ethane (6.87 mL, 55.1 mmol) and tetrabutylammonium iodide (0.407 g, 1.103 mmol) at 110° C. After stirring for 2.5 hr the mixture was cooled and the aqueous was decanted and the remaining sticky solid was dissolved in EtOAc. The organic was washed with H$_2$O and brine and dried over MgSO$_4$ and concentrated to leave a thick dark residue containing the desired product. The desired product was purified by flash chromatography on a silica column eluting with EtOAc/Hex 15% to 40% over 20 column volumes. The fractions containing the desired compound by TLC were combined and concentrated to provide 4-(4-bromo-2-isopropyl-1-(2-methyl-3-(trifluoromethyl)benzyl)-1H-benzo[d]imidazol-6-yl)morpholine (2.75 g, 4.99 mmol, 45.2% yield) as a light orange solid. MS (ES+) m/e: 495.1, 496.1 [M+H]+ e) (2-isopropyl-1-(2-methyl-3-(trifluoromethyl)benzyl)-6-morpholino-1H-benzo[d]imidazol-4-yl)boronic acid The titled compound was prepared from 4-(4-bromo-2-isopropyl-1-(2-methyl-3-(trifluoromethyl)benzyl)-1H-benzo[d]imidazol-6-yl)morpholine (1.01 g, 2.035 mmol) using a slightly modified Method B to give the desired product as described below.

A mixture of 4-(4-bromo-2-isopropyl-1-(2-methyl-3-(trifluoromethyl)benzyl)-1H-benzo[d]imidazol-6-yl)morpholine (1.01 g, 2.035 mmol), bis(pinacolato)diboron (1.550 g, 6.10 mmol), Pd$_2$(dba)$_3$ (0.093 g, 0.102 mmol), X-Phos (0.097 g, 0.203 mmol) and potassium acetate (0.599 g, 6.10 mmol) in 1,4-Dioxane (20 mL) in a 40 mL scintillation vial was heated for 1 hr at 95° C. When cooled, the reaction contents were poured into 1N HCl (3 ml) and H$_2$O (3 mL) mixture, swirled and then extracted with EtOAc, dried over MgSO$_4$ and concentrated in-vacuo. The residue was dissolved in MeOH and the material was purified by reverse phase chromatography eluting with a gradient 30% CH3CN to 60% CH3CN over 10 minutes. The fractions containing clean desired compound were combined and concentrated in vacuo to provide the desired product (178 mg, 0.386 mmol, 18.96% yield) as an off-white solid. Additional fractions, containing less pure desired product—contaminated with des-boronylated product as determined by LC/MS—were combined and the CH$_3$CN was removed in-vacuo leaving the material in H$_2$O. Upon standing a white solid fell out of the resulting solution. The white solid was collected by filtration, dried in a vacuum oven to yield (2-isopropyl-1-(2-methyl-3-(trifluoromethyl)benzyl)-6-morpholino-1H-benzo[d]imidazol-4-yl)boronic acid (296 mg, 0.642 mmol, 31.5% yield). The total yield of desired product was (474 mg, 1.03 mmol, 50.5% yield). MS (ES+) m/e: 461.2, 462.3 [M+H]$^+$; $^1$H NMR (400 MHz, METHANOL-d$_4$) δ ppm 7.67 (d, J=7.83 Hz, 1H), 7.47-7.60 (m, 1H), 7.27 (s, 1H), 7.10 (d, J=2.27 Hz, 1H), 6.63 (d, J=7.83 Hz, 1H), 5.85 (s, 2H), 3.72-3.85 (m, 4H), 3.57 (s, 1H), 3.10-3.24 (m, 4H), 2.62 (s, 3H), 1.45 (d, J=7.07 Hz, 6H).

Example 23

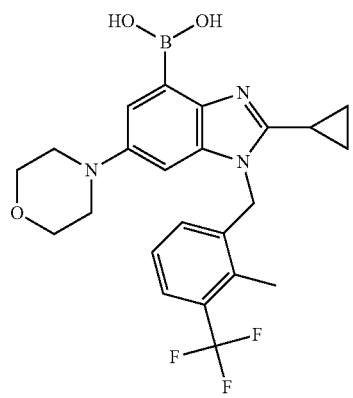 [SMILES: Cc1c(Cn2c(C3CC3)nc3c(B(O)O)cc(N4CCOCC4)cc32)cccc1C(F)(F)F]

Preparation of (2-cyclopropyl-1-(2-methyl-3-(trifluoromethyl)benzyl)-6-morpholino-1H-benzo[d]imidazol-4-yl)boronic acid

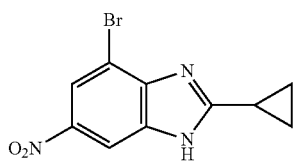 [SMILES: O=[N+]([O-])c1cc(Br)c2nc(C3CC3)[nH]c2c1]

a) 4-bromo-2-cyclopropyl-6-nitro-1H-benzo[d]imidazole

In a 250 mL round-bottom flask a mixture of 3-bromo-5-nitrobenzene-1,2-diamine (4 g, 17.24 mmol) and cyclopropanecarboxylic acid (14.06 ml, 155 mmol) in 3M HCl (40 ml, 120 mmol) was heated to 105° C. for 5 days. The mixture was allowed to cool to room temperature and was poured into chilled 5M NaOH (25 ml, 125 mmol) solution. The resulting mixture was allowed to stand in an icebath and the brown solid that precipitated was collected by filtration. The solid was washed several times with H$_2$O and then dried in a vacuum oven at 50° C. The resulting dark solid 4-bromo-2-cyclopropyl-6-nitro-1H-benzo[d]imidazole (4.3 g, 15.24 mmol, 88% yield) will be used as is in the next step. MS (ES+) m/e: 280.9, 281.8 [M+H]$^+$ b) 4-bromo-2-cyclopropyl-1-(2-methyl-3-(trifluoromethyl)benzyl)-6-nitro-1H-benzo[d]imidazole

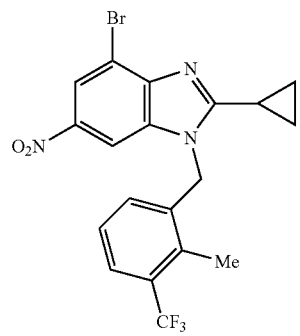 [SMILES: Cc1c(Cn2c(C3CC3)nc3c(Br)cc([N+](=O)[O-])cc32)cccc1C(F)(F)F]

To a 250 mL round bottomed flask containing DMF (50 mL) was added 4-bromo-2-cyclopropyl-6-nitro-1H-benzo[d]imidazole (4.3 g, 15.24 mmol), 1-(bromomethyl)-2-methyl-3-(trifluoromethyl)benzene (3.6 mL, 21.34 mmol) and potassium carbonate (6.32 g, 45.7 mmol). The resultant suspension was heated to 50° C. and after stirring for 30 minutes the mixture was allowed to cool to rt and diluted with 100 mL H$_2$O. The mixture was stirred overnight and the next day a brown filterable solid was isolated by filtration providing crude 4-bromo-2-cyclopropyl-1-(2-methyl-3-(trifluoromethyl)benzyl)-6-nitro-1H-benzo[d]imidazole (5.97 g, 13.14 mmol, 86% yield). MS (ES+) m/e: 453.0, 454.0 [M+H]+ c) 4-bromo-2-cyclopropyl-1-(2-methyl-3-(trifluoromethyl)benzyl)-1H-benzo[d]imidazol-6-amine

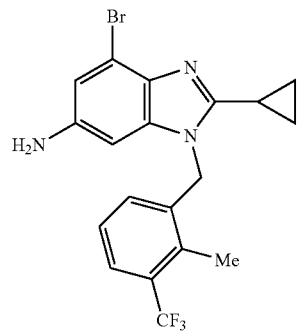

To a 250 mL round-bottom flask containing MeOH (70 mL) was added crude 4-bromo-2-cyclopropyl-1-(2-methyl-3-(trifluoromethyl)benzyl)-6-nitro-1H-benzo[d]imidazole (5.87 g, 12.92 mmol), tin(II) chloride dihydrate (8.75 g, 38.8 mmol) and hydrochloric acid (5.38 mL, 64.6 mmol). The resultant suspension was heated to 50° C. and monitored by LC/MS. By LC/MS analysis the reaction was complete in 30 minutes. After the reaction had cooled to rt, the majority of the MeOH was removed in-vacuo and sodium carbonate (64.6 mL, 64.6 mmol) was added slowly to adjust the pH to about 10 and the mixture was extracted with Et$_2$O (3×100 mL) and the organic was washed with H$_2$O and brine and dried over MgSO$_4$ and filtered. The solvent was removed in-vacuo leaving the desired compound (3.42 g, 8.06 mmol, 62.4% yield) as crude brown solid that by LC/MS was sufficiently pure to use in the next step. NMR was consistent with desired product. MS (ES+) m/e: 423.1, 423.8 [M+H]+; 1H NMR (400 MHz, METHANOL-d$_4$) δ ppm 7.57 (d, J=7.83 Hz, 1H), 7.19 (t, J=7.83 Hz, 1H), 6.84-6.95 (m, 1H), 6.35-6.58 (m, 2H), 5.51 (s, 1H), 5.42 (s, 1H), 2.57 (s, 3H), 1.84-1.98 (m, 1H), 1.05-1.17 (m, 2H), 0.87-1.05 (m, 2H)

d) 4-(4-bromo-2-cyclopropyl-1-(2-methyl-3-(trifluoromethyl)benzyl)-1H-benzo[d]imidazol-6-yl)morpholine

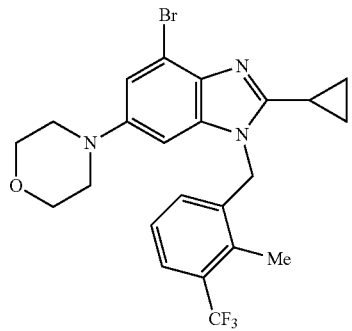 [SMILES: Cc1c(Cn2c(C3CC3)nc3c(Br)cc(N4CCOCC4)cc32)cccc1C(F)(F)F]

4-bromo-2-cyclopropyl-1-(2-methyl-3-(trifluoromethyl) benzyl)-1H-benzo[d]imidazol-6-amine (3.42 g, 8.06 mmol) was stirred in 6M sodium hydroxide (70 mL, 420 mmol) solution with 1-bromo-2-(2-bromoethoxy)ethane (5.03 mL, 40.3 mmol) and tetrabutylammonium iodide (0.298 g, 0.806 mmol) at 110° C. After stirring for 2.5 hr the mixture was cooled and the aqueous was decanted and the remaining sticky solid was dissolved in Et$_2$O/EtOAc. The organic was washed with H$_2$O and brine and dried over MgSO$_4$ and concentrated to leave a thick dark residue containing the desired product. The desired product was dissolved in CHCl$_3$, loaded onto a silica column, and was purified by flash chromatography eluting with EtOAc/Hex 20% to 40% over 20 column volumes. The fractions containing the desired compound by TLC were combined and concentrated and the resultant dark oil was triturated with Et$_2$O/Hexanes to provide 4-(4-bromo-2-cyclopropyl-1-(2-methyl-3-(trifluoromethyl)benzyl)-1H-benzo[d]imidazol-6-yl)morpholine (1.62 g, 3.28 mmol, 40.7% yield) as a light orange solid. MS (ES+) m/e: 495.1, 495.8 [M+H]+ e) (2-cyclopropyl-1-(2-methyl-3-(trifluoromethyl) benzyl)-6-morpholino-1H-benzo[d]imidazol-4-yl) boronic acid The titled compound was prepared from 4-(4-bromo-2-cyclopropyl-1-(2-methyl-3-(trifluoromethyl)benzyl)-1H-benzo[d]imidazol-6-yl)morpholine (1.01 g, 2.035 mmol) using a slightly modified Method B, to give the desired product (196 mg, 0.427 mmol, 20.9% yield) as described below.

A mixture of 4-(4-bromo-2-cyclopropyl-1-(2-methyl-3-(trifluoromethyl)benzyl)-1H-benzo[d]imidazol-6-yl)morpholine (1.01 g, 2.043 mmol), bis(pinacolato)diboron (1.556 g, 6.13 mmol), Pd2(dba)$_3$ (0.094 g, 0.102 mmol), X-Phos (0.097 g, 0.204 mmol) and potassium acetate (0.602 g, 6.13 mmol) in 1,4-Dioxane (20 mL) in a 40 mL scintillation vial was heated for 1 hr at 95° C. When cooled the reaction contents were poured into 1N HCl (10 ml) and H$_2$O (10 mL) mixture, swirled and then extracted with EtOAc, dried over MgSO$_4$ and concentrated in-vacuo. The residue was dissolved in MeOH and the material was purified by reverse phase chromatography eluting with a gradient 30% CH$_3$CN to 60% CH$_3$CN over 10 minutes. The fractions containing clean desired compound were combined and concentrated in-vacuo to provide the desired product (196 mg, 0.427 mmol, 20.89% yield) as a clear oil after drying in a vacuum oven at 50° C. The oil was triturated to provide an analytically pure off-white powder (2-cyclopropyl-1-(2-methyl-3-(trifluoromethyl)benzyl)-6-morpholino-1H-benzo[d]imidazol-4-yl)boronic acid (115 mg, 0.250 mmol, 12.26% yield). m/e: 459.2, 460.3 [M+H]+; $^1$H NMR (400 MHz, METHANOL-d$_4$) δ ppm 7.67 (d, J=8.08 Hz, 1H), 7.50 (br. s., 1H), 7.28 (t, J=7.83 Hz, 1H), 7.08 (d, J=2.27 Hz, 1H), 6.73 (d, J=8.08 Hz, 1H), 5.90 (s, 2H), 3.72-3.92 (m, 4H), 3.10-3.23 (m, 4H), 2.21-2.42 (m, 1H), 1.22-1.37 (m, 4H).

Biological Assays

Compounds of the present invention were tested according to the following assays and found as inhibitors of PI3 kinases, particularly PI3Kβ. The activities (IC$_{50}$) of exemplified compounds range from about 1 nM to about 10 μM against PI3Kβ. The majority of the compounds were under 500 nM; the most active compounds were under 10 nM. The IC$_{50}$ value can be converted and presented as pIC$_{50}$ value.

HTRF In Vitro Profiling Assays for PI3K Inhibition

The PI3-Kinase profiling assays were developed to measure the compound-dependent inhibition of the alpha, beta, delta, and gamma isoforms of PI3K in an in vitro catalytic assay. This assay was developed and optimized from a kit produced by Upstate (Millipore catalog #33-017). Briefly, this procedure utilizes a pre-formed HTRF (Homogeneous Time-Resolved Fluorescence energy transfer) complex between four binding partners: 1) biotinylated PIP3, 2) GST tagged pleckstrin homology (PH) domain, 3) Europium labeled anti-GST monoclonal antibody, and 4) Streptavidin-Allophycocyanin (APC). The native PIP3 produced by PI 3-Kinase activity displaces biotin-PIP3 from the PH domain, resulting in the dissociation of the HTRF complex and a decrease in the fluorescence signal. The format of this assay is the same for all 4 isoforms of PI3K; the differences lie in the concentration of enzyme used to achieve the most robust signal. The alpha and delta assays are run at 400 pM enzyme; the beta assay is at 200 pM enzyme and the gamma assay is run at 1 nM enzyme. In addition, the alpha, beta and delta assays are run with 150 mM NaCl while the gamma assay is run in the absence of NaCl. The ATP concentration is 100 uM in the alpha, beta, and delta assays and 15 uM ATP in the gamma assay. All reactions are run at 10 uM PIP2

Compounds were serially diluted (3-fold in 100% DMSO) across a 384-well polypropylene mother plate from column 1 to column 12 and column 13 to column 24, to yield 11 concentrations for each test compound. Columns 6 and 18 contain only DMSO. Once titrations were made, 0.05 μL was transferred to a 384-well low-volume assay plate (Greiner 784076). This assay plate contained three pharmacological controls (known PI3K inhibitors) and 3 assay controls: (1) Enzyme without inhibitor; (2) Buffer minus enzyme, and (3) Buffer minus enzyme plus native PIP3. DMSO was stamped into all wells of columns 6 and 18. PIP3 was added at 40 µM in 1× Reaction buffer (1 µL of 200 µM PIP3) to alternating rows of column 18 (wells 18 B, D, F, H, J, L, N, P). The no-enzyme control reactions were run in wells 18 A, C, E, G, I, K, M, O (0.1 µL of 100% DMSO).

The PI3-Kinase profiling assay was optimized using the HTRF kit provided by Upstate (Millipore). The assay kit contained seven reagents: 1) 4× Reaction Buffer; 2) native PIP2 (substrate); 3) Stop A (EDTA); 4) Stop B (Biotin-PIP3); 5) Detection Mix A (Streptavidin-APC); 6) Detection Mix B (Eu-labeled Anti-GST plus GST-tagged PH-domain); 7) Detection Mix C (KF). In addition, the following items were obtained or purchased: PI3Kinase (prepared by GSK BR&AD), dithiothreitol (Sigma, D-5545), Adenosine-5'-triphosphate (ATP, Teknova cat. # A0220), native PIP3 (1,2-dioctanoyl-sn-glycero-3-[phosphoinositil-3,4,5-triphosphate]tetraammonium salt (Avanti polar lipids, 850186P), DMSO (Sigma, 472301).

PI3Kinase Reaction Buffer was prepared by diluting the stock 1:4 with de-ionized water. Freshly prepared DTT was added at a final concentration of 5 mM on the day of use. Enzyme addition and compound pre-incubation were initiated by the addition of 2.5 µL of PI3K (at twice its final concentration) in 1× reaction buffer to all wells using a Multidrop Combi. Plates were incubated at room temperature for 15 minutes. Reactions were initiated by addition of 2.5 µL of 2× substrate solution (PIP2 and ATP in 1× reaction buffer) using a Multidrop Combi. Plates were incubated at room temperature for one hour. Reactions were quenched by the addition of 2.5 µL of stop solution (Stop A and Stop B premixed at a ratio of 5:1, respectively) to all wells using the Multidrop Combi. The quenched reactions were then processed to detect product formation by adding 2.5 µL of Detection Solution to all wells using the Mulitdrop Combi (Detection mix C, Detection mix A, and Detection mix B combined together in an 18:1:1 ratio, i.e.: for a 6000 µL total volume, mix 5400 µL Detection mix C, 300 µL Detection mix A, and 300 µL Detection mix B. Note: this solution should be prepared 2 hours prior to use). Following a one hour incubation in the dark, the HTRF signal was measured on the Envision plate reader set for 330 nm excitation and dual emission detection at 620 nm (Eu) and 665 nm (APC).

The loss of the HTRF signal is due to the displacement of biotinylated-PIP3 from the PH domain by the PI3K-dependent conversion of PIP2 to PIP3. This loss of signal is non-linear with respect to both increasing product and time. This non-linear detection will impact accuracy of $IC_{50}$ calculations; therefore, there is a need for a correction factor to obtain more accurate $IC_{50}$ values. This correction is derived from the assay standards in the wells of column 6 and 18 of the assay plate.

All data were calculated using the ratio of acceptor (APC) to donor (Europium) fluorescence in each well of the assay plate. The percent inhibition for each compound concentration was calculated as follows: % inhibition=100*(fluorescence ratio−CtrlB)/(CtrlA−CtrlB) where CtrlA=(−) PI3Kinase reaction and CrtlB=PI3Kinase+DMSO.

An $IC_{50}$ was then calculated fitting the % inhibition data to the equation: % inhibition=min+(max−min)/(1+([inhibitor]/$IC_{50}$^n) where min is the % inhibition with no inhibitor (typically 0%), max is the signal in the (−) Enzyme control, and n is the Hill slope (typically 1). Finally, the $IC_{50}$ was converted to $pIC_{50}$ ($pIC_{50}$=−log($IC_{50}$)), and the $pIC_{50}$ value was corrected by using plate controls and the equation below: $pIC_{50}$ (corrected)=$pIC_{50}$ (observed)+log 10((CtrlA−CtrlB)/(CtrlB−CtrlC)), where CtrlA and CtrlB are as defined above and CrtlC=10 µM PI(3,4,5)P3, 100% displacement of biotinylated PI(3,4,5)P3.

The compounds listed in Table 1 were tested generally according to the assays described herein. Table 1 lists the $pIC_{50}$ values for either an experimental run or an average of two or more experimental runs with the examples shown.

TABLE 1

| Example # | MW | PI3K b $pIC_{50}$ |
|---|---|---|
| 4 | 433.24 | 9.4 |
| 5 | 399.69 | 9.7 |
| 6 | 401.28 | 9.3 |
| 7 | 379.27 | 9.3 |
| 8 | 420.11 | 9.3 |
| 9 | 407.30 | 8.9 |
| 10 | 365.24 | 7.2 |
| 11 | 365.24 | 8.0 |
| 12 | 385.66 | 7.4 |
| 13 | 385.66 | 7.2 |
| 14 | 419.22 | 8.8 |
| 15 | 385.66 | 8.9 |
| 16 | 451.23 | 10.2 |
| 17 | 417.68 | 10.2 |
| 18 | 449.24 | 9.7 |
| 19 | 435.67 | 10.1 |
| 20 | 469.22 | 9.9 |
| 21 | 453.66 | 10.1 |
| 22 | 461.30 | 8.5 |
| 23 | 459.28 | 8.9 |

Cellular Assays—Inhibition of Phosphorylation of AKT in PTEN Deficient Tumor Cell Line MDA-MB-468

Compounds were evaluated for their ability to inhibit downstream phosphorylation of AKT in MDA-MB-468 tumor cells. Breast cancer cells were plated, incubated for approximately 16-20 hours and then treated with compound for 30 minutes. Final DMSO concentration on all cells was 0.15%. The cells were washed with Tris buffer and lysed in MesoScale Discovery (MSD) lysis buffer containing protease and phosphatase inhibitors (included in MSD kit). MSD Ser473-AKT duplex plates (Cat # MS6000) were used according to the manufacturer's instructions and plates were read on a SECTOR™ Imager 6000 using MSD Workbench software. For analysis of the Ser473-pAKT concentration response curves, the data was normalized using the corresponding total AKT value (sum of pAKT and AKT signal) and plotted as the percent of the DMSO-treated control values. The data was fit in Graphpad Prism version 4 for Windows (Graphpad Software, San Diego, Calif.).

The compounds listed in Table 2 were tested generally according to the assays described herein. Table 2 lists the $IC_{50}$ values for either an experimental run or an average of two or more experimental runs with the examples shown.

TABLE 2

| Example # | MW | $IC_{50}$ pAKT (nM) MDA-MB-468 |
|---|---|---|
| 4 | 433.24 | 18.7 |
| 5 | 399.69 | 8.97 |
| 6 | 401.28 | 78.25 |
| 7 | 379.27 | 45.63 |
| 8 | 420.11 | 61.05 |
| 9 | 407.30 | 65.85 |
| 10 | 365.24 | 672.25 |
| 11 | 365.24 | 227.08 |
| 12 | 385.66 | 1490 |
| 13 | 385.66 | 104.6 |
| 14 | 419.22 | 24.35 |

TABLE 2-continued

| Example # | MW | IC$_{50}$ pAKT (nM) MDA-MB-468 |
|---|---|---|
| 15 | 385.66 | 7.95 |
| 16 | 451.23 | 19.1 |
| 17 | 417.68 | 14.5 |
| 18 | 449.24 | 6.35 |
| 19 | 435.67 | 70.9 |
| 20 | 469.22 | 40.1 |
| 21 | 453.66 | 92.9 |
| 22 | 461.30 | 74.6 |
| 23 | 459.28 | 56.2 |

Cellular Assays—Cell Growth Inhibition in PTEN-Deficient Cell Line MDA-MB-468

PTEN deficient tumor cell lines (MDA-MB-468) were cultured generally according to instructions supplied by cell culture supplier American Type Culture Collection, Manassas, Va., with 10% fetal bovine serum at 5% CO$_2$ and 37° C. Cells were seeded into either a T-75 or a T-175 flask 3-4 days prior to 96-well assay plating such that the flasks were approximately 70-80% confluent of the time of harvest. Cells were harvested using 0.25% trypsin-EDTA (Invitrogen #25200056). Trypan Blue exclusion staining was used to determine cell number.

Viable cells were plated in clear, flat bottom 96-well plates (BD #353075) under anchorage independent conditions at 2,000-10,000 cells per well depending on the cell line. To generate anchorage independent growth conditions, a 5% agar stock solution in water was made and autoclaved to melt and sterilize. From the 5% agar solution, a 0.6% agar/media+10% fetal bovine serum (FBS) solution was made to generate a bottom agar layer in the plates to prevent cell attachment. Seventy five microliters per well of the 0.6% agar-media solution was added to the plates. After solidification, a cell solution of 266,870 to 1,334,022 cells (depending on the cell line) in 10 ml of 0.3% agar/media+10% FBS was made and 75 μl of the cell/media/agar suspension was added to the plates. After the cell layer solidified, 50 μl of media+10% FBS was added to the top of the cells. A 0.3% Brij 35 (Sigma B4184) solution in media+10% FBS was added to column 12 as a background subtraction control. The cells were incubated overnight at 5% CO$_2$ and 37° C. The next day one plate of cells was processed at the time of compound addition to quantify the starting number of cells (T=0 or T0).

To generate the compound titration plates, 15 μl of a 2 mM or 20 μl of a 20 mM solution of the compound of example 31 was diluted in clear bottom polypropylene 96-well plate (BD #351190) using a 10 point, 3-fold titration or a 20 point 2-fold titration, respectively. Three hundred microliters of media was added to the compound dilutions. Ten microliters per well of the serial dilutions was added to the cells and the plates incubated for 6 days at 5% CO$_2$ and 37° C. The final concentration of DMSO in all wells was 0.15% and the highest final concentration of the compound of example 31 was 3.7 μM or 30.7 μM.

Following the 6-day incubation, 20 μl of Alamar Blue (Invitrogen #DAL1100) was added to the cells, incubated at 5% CO$_2$ and 37° C. for 6 hours and the plates read on a Spectramax (Gemini EM) at 530 nm (excitation) and 590 nm (emission) with the auto cut-off disabled. For analysis of cell growth inhibition dose response curves, the data was plotted as the percent of the DMSO-treated control samples (DMSO samples set to 100%). The cellular response was determined for compounds and control compounds by fitting the concentration response with a 4 parameter curve fit using XLfit software and determining the concentration that inhibits 50% of the Ymax-Ymin window (EC$_{50}$). The EC$_{50}$ is the midpoint of active compound effect window (between Ymax plateau and Ymin plateau of compound) and represents the concentration of the compound of example 31 where 50% of its maximal effect is observed. Values from wells containing 0.3% Brij 35 (under anchorage independent conditions) were subtracted from all samples for background correction.

The compounds listed in Table 3 were tested generally according to the assays described herein. Table 3 lists the EC$_{50}$ values for either an experimental run or an average of two or more experimental runs with the examples shown.

TABLE 3

| Example # | MW | Prolif EC$_{50}$ (nM) MDA-MB-468 |
|---|---|---|
| 4 | 433.24 | 11.1 |
| 5 | 399.69 | 6.7 |
| 6 | 401.28 | 22.3 |
| 7 | 379.27 | 18.3 |
| 8 | 420.11 | 42 |
| 9 | 407.30 | 88.2 |
| 10 | 365.24 | 1880 |
| 11 | 365.24 | 1135 |
| 12 | 385.66 | 3578 |
| 13 | 385.66 | 246 |
| 14 | 419.22 | 62.8 |
| 15 | 385.66 | 60 |
| 16 | 451.23 | 21.5 |
| 17 | 417.68 | 17.8 |
| 18 | 449.24 | 13.5 |
| 19 | 435.67 | 31.5 |
| 20 | 469.22 | 39.8 |
| 21 | 453.66 | 129.5 |
| 22 | 461.30 | 161.1 |
| 23 | 459.28 | 125.7 |

ADDITIONAL REFERENCES

The compounds of the present invention can also be tested to determine their inhibitory activity at PI3Kα, PI3Kδ, PI3Kβ and PI3Kγ according to international patent publication No. WO2009/039140.

The pharmaceutically active compounds within the scope of this invention are useful as PI3 Kinase inhibitors in mammals, particularly humans, in need thereof.

The present invention therefore provides a method of treating diseases associated with PI3 kinase inhibition, particularly: autoimmune disorders, inflammatory diseases, cardiovascular diseases, neurodegenerative diseases, allergy, asthma, pancreatitis, multiorgan failure, kidney diseases, platelet aggregation, cancer, sperm motility, transplantation rejection, graft rejection and lung injuries and other conditions requiring PI3 kinase modulation/inhibition, which comprises administering an effective compound of Formula (I) or a pharmaceutically acceptable salt, hydrate, solvate or prodrug thereof. The compounds of Formula (I) also provide for a method of treating the above indicated disease states because of their ability to act as PI3 inhibitors. The drug may be administered to a patient in need thereof by any conventional route of administration, including, but not limited to, intravenous, intramuscular, oral, subcutaneous, intradermal, and parenteral.

Exemplary Capsule Composition

An oral dosage form for administering the present invention is produced by filing a standard two piece hard gelatin capsule with the ingredients in the proportions shown in Table 3, below.

TABLE 3

| INGREDIENTS | AMOUNTS |
| --- | --- |
| Compound of example 1 | 25 mg |
| Lactose | 55 mg |
| Talc | 16 mg |
| Magnesium Stearate | 4 mg |

Exemplary Injectable Parenteral Composition

An injectable form for administering the present invention is produced by stirring 1.5% by weight of compound of example 1 in 10% by volume propylene glycol in water.

Exemplary Tablet Composition

The sucrose, calcium sulfate dihydrate and an PI3K inhibitor as shown in Table 4 below, are mixed and granulated in the proportions shown with a 10% gelatin solution. The wet granules are screened, dried, mixed with the starch, talc and stearic acid; screened and compressed into a tablet.

TABLE 4

| INGREDIENTS | AMOUNTS |
| --- | --- |
| Compound of example 1 | 20 mg |
| calcium sulfate dehydrate | 30 mg |
| Sucrose | 4 mg |
| Starch | 2 mg |
| Talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:

1. A compound of formula (I):

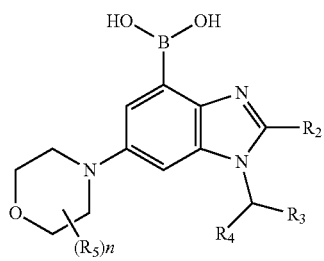

(I)

wherein

R2 is selected from H, —NHRa, alkoxy, halogen, —CF$_3$, —CHF$_2$, and C$_{1-6}$alkyl;

R3 is selected from aryl and heteroaryl, wherein said aryl or heteroaryl may be substituted by one to three Rc;

R4 is selected from H or Ra;

each R5 is independently selected from C$_{1-6}$alkyl;

each Ra is independently selected from C$_{1-3}$alkyl;

each Rc is independently selected from C$_{1-3}$alkyl, halogen, —CF$_3$, and hydroxy; and n is 0-2, or a pharmaceutically acceptable salt thereof.

2. The compounds of claim 1, having the formula (I)(A)

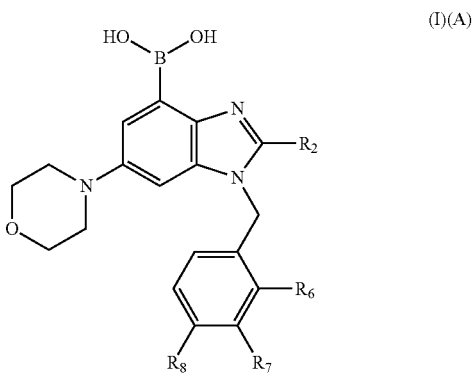

(I)(A)

wherein

R2 is selected from H, —NHRa, alkoxy, —CH$_2$Rc, —CH(Rc)$_2$, —CF$_3$, or C$_{1-6}$alkyl;

each of R6, R7, and R8 is independently selected from C$_{1-3}$alkyl, halogen, —CF$_3$, and hydroxyl, or R6 and R7 combine to form a bi-cyclic aryl or heteroaryl, or R7 and R8 combine to form a bi-cyclic aryl or heteroaryl;

each Ra is independently selected from C$_{1-3}$alkyl; and each Rc is selected from CH$_3$ and F;

or a pharmaceutically acceptable salt thereof.

3. The compounds of claim 1, having the Formula (I)(B)

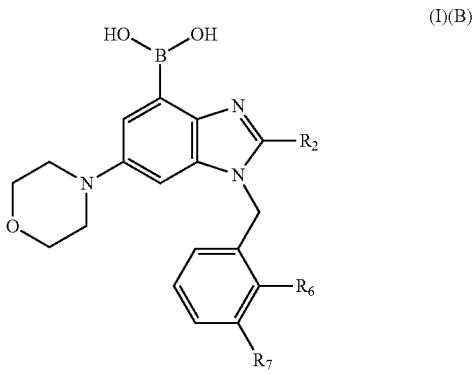

(I)(B)

wherein

R2 is selected from H, —CH$_2$Rc, —CH(Rc)$_2$, —CF$_3$, or C$_{1-6}$alkyl;

each of R6 and R7 is independently selected from C$_{1-3}$alkyl, halogen, and —CF$_3$, or R6 and R7 combine to form a bi-cyclic aryl or heteroaryl; and each Rc is selected from CH$_3$ and F;

or a pharmaceutically acceptable salt thereof.

4. The compounds of claim 3, wherein R6 and R7 combine to form a naphthal or an indole.

5. The compounds of claim 3, wherein R6 and R7 are independently selected from C$_{1-3}$alkyl, halogen, and —CF$_3$.

6. A compound selected from 4-(4-bromo-2-methyl-1H-benzo[d]imidazol-6-yl)morpholine;

4-(4-bromo-1-(3-chloro-2-methylbenzyl)-2-methyl-1H-benzo[d]imidazol-6-yl)morpholine;

4-(4-bromo-2-methyl-1-(2-methyl-3-(trifluoromethyl)benzyl)-1H-benzo[d]imidazol-6-yl)morpholine;

(2-methyl-1-(2-methyl-3-(trifluoromethyl)benzyl)-6-morpholino-1H-benzo[d]imidazol-4-yl)boronic acid;
(1-(3-chloro-2-methylbenzyl)-2-methyl-6-morpholino-1H-benzo[d]imidazol-4-yl)boronic acid;
(2-methyl-6-morpholino-1-(naphthalen-1-ylmethyl)-1H-benzo[d]imidazol-4-yl)boronic acid;
(1-(2,3-dimethylbenzyl)-2-methyl-6-morpholino-1H-benzo[d]imidazol-4-yl)boronic acid;
(1-(2,3-dichlorobenzyl)-2-methyl-6-morpholino-1H-benzo[d]imidazol-4-yl)boronic acid;
4-(1-(benzo[b]thiophen-7-ylmethyl)-4-bromo-2-methyl-1H-benzo[d]imidazol-6-yl)morpholine;
(2-methyl-1-(3-methylbenzyl)-6-morpholino-1H-benzo[d]imidazol-4-yl)boronic acid;
(2-methyl-1-(2-methylbenzyl)-6-morpholino-1H-benzo[d]imidazol-4-yl)boronic acid;
(1-(2-chlorobenzyl)-2-methyl-6-morpholino-1H-benzo[d]imidazol-4-yl)boronic acid;
(1-(3-chlorobenzyl)-2-methyl-6-morpholino-1H-benzo[d]imidazol-4-yl)boronic acid;
(1-(2-methyl-3-(trifluoromethyl)benzyl)-6-morpholino-1H-benzo[d]imidazol-4-yl)boronic acid;
(1-(3-chloro-2-methylbenzyl)-6-morpholino-1H-benzo[d]imidazol-4-yl)boronic acid;
(2-(fluoromethyl)-1-(2-methyl-3-(trifluoromethyl)benzyl)-6-morpholino-1H-benzo[d]imidazol-4-yl)boronic acid;
(1-(3-chloro-2-methylbenzyl)-2-(fluoromethyl)-6-morpholino-1H-benzo[d]imidazol-4-yl)boronic acid;
(2-(hydroxymethyl)-1-(2-methyl-3-(trifluoromethyl)benzyl)-6-morpholino-1H-benzo[d]imidazol-4-yl)boronic acid;
(1-(3-chloro-2-methylbenzyl)-2-(difluoromethyl)-6-morpholino-1H-benzo[d]imidazol-4-yl)boronic acid;
(2-(difluoromethyl)-1-(2-methyl-3-(trifluoromethyl)benzyl)-6-morpholino-1H-benzo[d]imidazol-4-yl)boronic acid;
(1-(3-chloro-2-methylbenzyl)-6-morpholino-2-(trifluoromethyl)-1H-benzo[d]imidazol-4-yl)boronic acid;
(2-isopropyl-1-(2-methyl-3-(trifluoromethyl)benzyl)-6-morpholino-1H-benzo[d]imidazol-4-yl)boronic acid; and
(2-cyclopropyl-1-(2-methyl-3-(trifluoromethyl)benzyl)-6-morpholino-1H-benzo[d]imidazol-4-yl)boronic acid,
or a pharmaceutically acceptable salt thereof.

7. A method for treating a PTEN-deficient neoplasm selected from brain (gliomas), glioblastomas, leukemias, Bannayan-Zonana syndrome, Cowden disease, Lhermitte-Duclos disease, breast cancer, inflammatory breast cancer, colorectal cancer, Wilm's tumor, Ewing's sarcoma, Rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T cell, leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, Plasmacytoma, Immunoblastic large cell leukemia, Mantle cell leukemia, Megakaryoblastic leukemia, multiple myeloma, Acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer in a mammal in need thereof, said method comprising administering to the mammal a therapeutically effective amount of a compound according to claim 1.

8. The method according to claim 7, wherein said PTEN-deficient neoplasm is selected from hormone refractory prostate cancer, non-small-cell lung cancer, endometrial cancer, gastric cancer, melanoma, head and neck cancer, breast cancer, including trip-negative breast cancer, and glioma.

9. The method according to claim 7, wherein said mammal is a human.

* * * * *